US009339407B2

(12) United States Patent
Bhat et al.

(10) Patent No.: US 9,339,407 B2
(45) Date of Patent: May 17, 2016

(54) APPARATUS AND METHODS FOR CONFORMING A SUPPORT TO A BODY

(71) Applicants: Nikhil Bhat, Fremont, CA (US); George Y. Choi, Atherton, CA (US); Allen Li, San Francisco, CA (US); Jasper Jackson, Newark, CA (US); Stuart Lin, Daly City, CA (US)

(72) Inventors: Nikhil Bhat, Fremont, CA (US); George Y. Choi, Atherton, CA (US); Allen Li, San Francisco, CA (US); Jasper Jackson, Newark, CA (US); Stuart Lin, Daly City, CA (US)

(73) Assignee: PRS Medical Technologies, Inc., Atherton, CA (US)

( * ) Notice: Subject to any disclaimer, the term of this patent is extended or adjusted under 35 U.S.C. 154(b) by 287 days.

(21) Appl. No.: 13/683,198

(22) Filed: Nov. 21, 2012

(65) Prior Publication Data

US 2013/0112213 A1 May 9, 2013

Related U.S. Application Data

(63) Continuation-in-part of application No. 13/407,628, filed on Feb. 28, 2012, now Pat. No. 8,656,919, which is a continuation-in-part of application No. 13/189,320, filed on Jul. 22, 2011, now Pat. No. 8,776,798.

(51) Int. Cl.
*A47C 7/00* (2006.01)
*A47C 21/04* (2006.01)
(Continued)

(52) U.S. Cl.
CPC ... *A61F 5/34* (2013.01); *A47C 3/12* (2013.01); *A47C 4/54* (2013.01); *A47C 7/02* (2013.01); *A47C 7/021* (2013.01); *A47C 7/022* (2013.01); *A47C 27/00* (2013.01); *A47C 27/08* (2013.01); *A47C 27/081* (2013.01); *A47C 27/083* (2013.01); *A47C 27/085* (2013.01); *A47C 27/10* (2013.01); *A61F 5/00* (2013.01); *A61F 5/01* (2013.01); *A61F 5/30* (2013.01);
(Continued)

(58) Field of Classification Search
CPC .............. A47C 3/12; A47C 4/54; A47C 7/02; A47C 7/021; A47C 7/022; A47C 27/00; A47C 27/08; A47C 27/081; A47C 27/083; A47C 27/085; A47C 27/10; A61F 5/00; A61F 5/01; A61F 5/30; A61F 5/32; A61F 5/34
USPC .............. 5/421, 422, 636, 637, 640, 643, 644, 5/645, 713, 714, 733; 128/96.1, 98.1, 128/99.1, 106.1, 112.1, 116.1, 118.1, 845, 128/846, 869, 870, 889, 891
See application file for complete search history.

(56) References Cited

U.S. PATENT DOCUMENTS

| | | | |
|---|---|---|---|
| 3,748,669 A | 7/1973 | Warner | |
| 4,175,548 A | 11/1979 | Henry | |

(Continued)

FOREIGN PATENT DOCUMENTS

| | | |
|---|---|---|
| WO | WO 2007/047379 | 4/2007 |
| WO | WO 2013/016241 | 1/2013 |
| WO | WO 2014/081521 | 5/2014 |

*Primary Examiner* — Alireza Nia
*Assistant Examiner* — Brandon L Jackson
(74) *Attorney, Agent, or Firm* — Levine Bagade Han LLP

(57) ABSTRACT

Apparatus and methods for conforming a support to a body are described in which a portable support assembly may be worn by a bed-stricken individual around particular regions of the body where pressure ulcers tend to form. The portable support assembly may generally include adjustable supports which conform the assembly to the patient's body and which also help to distribute one or more fluid pad assemblies relative to the body.

43 Claims, 19 Drawing Sheets

(51) Int. Cl.

| | | |
|---|---|---|
| *A47C 20/00* | (2006.01) | |
| *A47C 20/02* | (2006.01) | |
| *A47C 27/08* | (2006.01) | |
| *A47C 17/00* | (2006.01) | |
| *A61F 5/24* | (2006.01) | |
| *A61F 5/28* | (2006.01) | |
| *A61F 5/30* | (2006.01) | |
| *A61F 5/32* | (2006.01) | |
| *A61F 5/34* | (2006.01) | |
| *A61G 15/00* | (2006.01) | |
| *A61F 5/37* | (2006.01) | |
| *A61B 19/00* | (2006.01) | |
| *A61F 13/00* | (2006.01) | |
| *A61F 5/00* | (2006.01) | |
| *A47C 7/02* | (2006.01) | |
| *A47C 27/10* | (2006.01) | |
| *A47C 3/12* | (2006.01) | |
| *A47C 27/00* | (2006.01) | |
| *A61F 5/01* | (2006.01) | |
| *A47C 4/54* | (2006.01) | |
| *A61G 7/057* | (2006.01) | |
| *A61G 7/07* | (2006.01) | |

(52) U.S. Cl.
CPC .. *A61F 5/32* (2013.01); *A61F 5/37* (2013.01); *A61G 7/05769* (2013.01); *A61G 7/07* (2013.01)

(56) References Cited

U.S. PATENT DOCUMENTS

| | | | |
|---|---|---|---|
| 4,483,030 A | 11/1984 | Flick et al. | |
| 4,534,078 A | 8/1985 | Viesturs et al. | |
| 4,559,933 A | 12/1985 | Batard et al. | |
| 4,617,690 A | 10/1986 | Grebe | |
| 4,622,957 A | 11/1986 | Curlee | |
| 4,673,605 A | 6/1987 | Sias et al. | |
| 4,682,588 A | 7/1987 | Curlee | |
| 4,726,624 A | 2/1988 | Jay | |
| 4,836,194 A | 6/1989 | Sebastian et al. | |
| 4,934,002 A | 6/1990 | Watanabe | |
| 5,040,525 A | 8/1991 | Georgijevic | |
| 5,122,111 A | 6/1992 | Sebastian et al. | |
| 5,144,705 A | 9/1992 | Rogers | |
| 5,152,023 A | 10/1992 | Graebe | |
| 5,303,436 A | 4/1994 | Dinsmoor, III et al. | |
| 5,388,292 A | 2/1995 | Stinson et al. | |
| 5,421,874 A | 6/1995 | Pearce | |
| 5,489,259 A | 2/1996 | Jacobs et al. | |
| 5,671,552 A | 9/1997 | Pettibone et al. | |
| 5,794,289 A | 8/1998 | Wortman et al. | |
| 5,829,081 A | 11/1998 | Pearce | |
| 6,012,188 A | 1/2000 | Daniels et al. | |
| 6,020,055 A | 2/2000 | Pearce | |
| 6,026,527 A | 2/2000 | Pearce | |
| 6,047,425 A * | 4/2000 | Khazaal | 5/644 |
| 6,065,166 A | 5/2000 | Sharrock et al. | |
| 6,197,099 B1 | 3/2001 | Pearce | |
| 6,216,299 B1 | 4/2001 | Kohlman | |
| 6,560,803 B2 | 5/2003 | Zur | |
| 6,640,367 B2 * | 11/2003 | Hsia | 5/640 |
| 6,813,790 B2 | 11/2004 | Flick et al. | |
| 6,874,185 B1 | 4/2005 | Phillips et al. | |
| 6,896,662 B2 | 5/2005 | Heffez | |
| 7,060,213 B2 | 6/2006 | Pearce | |
| 7,063,677 B1 | 6/2006 | Daggett | |
| 7,141,032 B2 | 11/2006 | Flam et al. | |
| 7,216,388 B2 | 5/2007 | Bieganek et al. | |
| 7,254,852 B2 | 8/2007 | Martin | |
| 8,656,919 B2 | 2/2014 | Bhat et al. | |
| 2003/0041379 A1 | 3/2003 | Habboub et al. | |
| 2003/0120191 A1 | 6/2003 | Clement | |
| 2005/0177952 A1 | 8/2005 | Wilkinson et al. | |
| 2006/0010607 A1* | 1/2006 | Schneider | 5/713 |
| 2007/0063368 A1 | 3/2007 | Schindler | |
| 2008/0249449 A1 | 10/2008 | Brown et al. | |
| 2009/0070939 A1 | 3/2009 | Hann | |
| 2009/0095566 A1 | 4/2009 | Leong et al. | |
| 2009/0194115 A1 | 8/2009 | Squitieri | |
| 2009/0254015 A1 | 10/2009 | Segal et al. | |
| 2010/0152821 A1 | 6/2010 | Rein et al. | |
| 2010/0229308 A1 | 9/2010 | Pearce et al. | |
| 2010/0242182 A1 | 9/2010 | Chuang et al. | |
| 2011/0099714 A1 | 5/2011 | Svoboda | |
| 2011/0126356 A1 | 6/2011 | Steppat et al. | |
| 2011/0239372 A1 | 10/2011 | Bhat et al. | |
| 2012/0311787 A1 | 12/2012 | Purdy et al. | |
| 2013/0019873 A1 | 1/2013 | Choi et al. | |
| 2013/0019881 A1 | 1/2013 | Bhat et al. | |
| 2013/0092175 A1 | 4/2013 | Bhat et al. | |
| 2013/0174855 A1 | 7/2013 | Choi et al. | |
| 2013/0174856 A1 | 7/2013 | Choi et al. | |
| 2013/0174859 A1 | 7/2013 | Bhat et al. | |
| 2013/0180530 A1 | 7/2013 | Choi et al. | |
| 2013/0180531 A1 | 7/2013 | Choi et al. | |
| 2013/0255699 A1 | 10/2013 | Squitieri | |

* cited by examiner

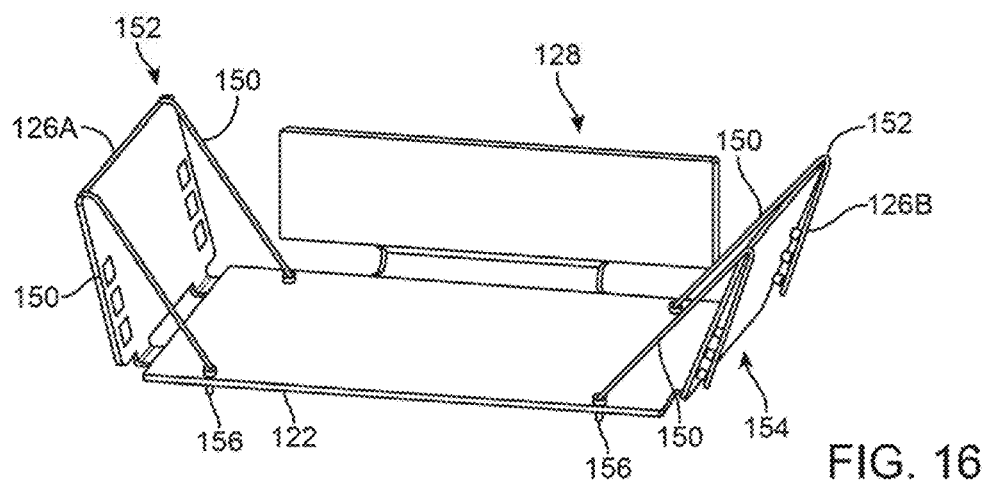
FIG. 16
FIG. 17A
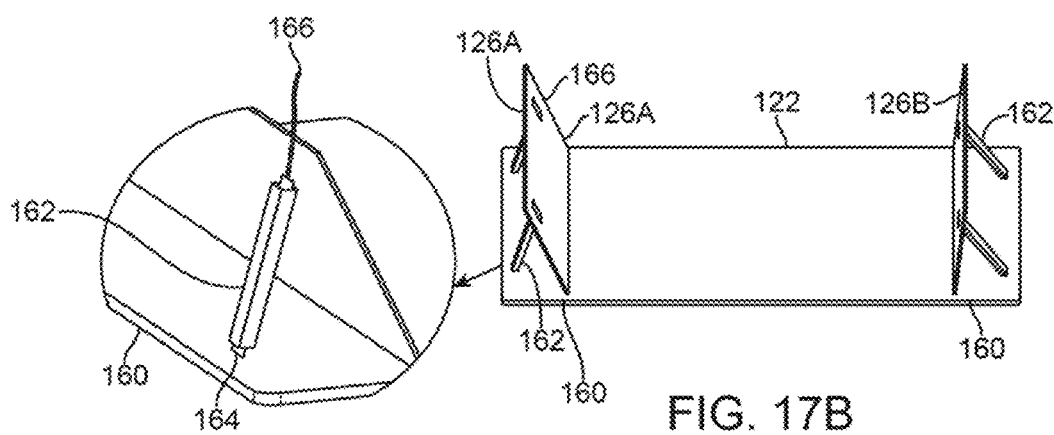
FIG. 17B
FIG. 17C

APPARATUS AND METHODS FOR CONFORMING A SUPPORT TO A BODY

This application is a continuation-in-part of U.S. application Ser. No. 13/407,628 filed Feb. 28, 2012 (now U.S. Pat. No. 8,656,919 issued Feb. 25, 2014), which is a continuation-in-part of U.S. application Ser. No. 13/189, 320 filed Jul. 22, 2011 (now U.S. Pat. No. 8,776,798 issued Jul. 15. 2014) each of which is incorporated herein by reference in its entirety.

FIELD OF THE INVENTION

The present invention relates to devices and methods for preventing and treating pressure ulcers. More particularly, the present invention relates to devices and methods for preventing and treating pressure ulcers with cushioning devices which are portable and easily conformed to various regions of the patient's body by utilizing, individual cushioning pods which are supported within an inner fluid pad as well as an outer fluid pad.

BACKGROUND OF THE INVENTION

Individuals who are forced to sit or lie down for extended periods of time typically experience tissue necrosis over localized regions of their body known as decubitus ulcers or pressure sores. These pressure ulcers generally occur at locations of the body where the bony prominence is high and the underlying skin breaks down when constant pressure is placed against the skin. Blood circulation is inhibited or prevented in these localized areas and can even occur when the patient has been lying against or upon cushioning devices. Examples of areas of the body where pressure sores typically occur include the sacrum, greater trochanter, ischial tuberosity, malleolus, heel, etc. When pressure ulcers form, they can lead to extensive stays in the hospital or even to amputation.

Conventional cushioning devices generally utilize flexible materials such as foam or springs which allow for the cushion to deform and conform to the patient's body. While the cushioning device attempts to redistribute the loading from localized regions of the patient's body to a larger area over the rest of the body, such devices typically bottom out such that the patient's body contacts the underlying platform and nonetheless localizes the pressure onto the body.

Other cushioning devices have utilized fluid-filled cushions which consist of lame single bladders or compartmentalized fluid or gas-filled bladders which inhibit fluid contained within the bladders from flowing laterally. Such fluid-filled cushions attempt to hammock or suspend the patient's body while preventing the patient's body from bottoming out. However, such devices typically require a large area for placement beneath the patient or require specialized bedding.

Yet other cushioning devices utilize segmented bladders in an attempt to isolate individual bladders from one another. Yet such segmented cushions may fail to allow for the cushion to fully conform to the patient's body as fluid between each of the segmented cushions is prevented.

Accordingly, there exists a need for a cushioning device which may conform to regions of the patient's body to prevent decubitis ulcers in a manner which is more cost efficient, convenient, and effective.

BRIEF SUMMARY OF THE INVENTION

A portable support assembly may be worn by an individual who may be bed-stricken for an extended period of time to prevent the formation of pressure ulcers. Such a portable support assembly may be worn by the individual around particular regions of the body where pressure ulcers tend to form, e.g., sacrum, trochanter, ischium, as well as any other region of the body where support is desired. The portable support assembly may be formed into an elongated shape to be wrapped entirely around the patient's body, e.g., around the hips or lower back, or a portion of the body, e.g., around the ankles or feet. Alternatively, the support assembly may be placed upon a bed or platform or directly integrated into the bed or platform) upon which the patient is resting.

The support assembly may be configured to be portable such that it may be worn directly over or upon the patient's body independently from the underlying bed or cushion. Accordingly, the patient may utilize the support assembly on any underlying bed or platform. Additionally, while the examples described illustrate portable support assemblies, the support assembly may be integrated into a bed, underlying cushion, and/or mattress pad if so desired and as previously described.

Generally, the support assembly may comprise one or more pods positioned adjacent to one another, an inner pad enclosing the one or more pods such that compression of the pods is controlled by the inner pad, an outer pad enclosing the inner pad, and an outer shell attached to the outer pad, wherein the outer shell is sufficiently flexible to be worn upon a portion of a subject's body.

In use, the support assembly may support the desired region of the body by securing a portable support assembly directly to the region of the body to be supported, controlling displacement of one or more pods positioned along the support assembly beneath the region via an inner pad enclosing the one or more pods, and redistributing a pressure load from the one or more pods and inner pad to an outer pad positioned along the support assembly and enclosing, the inner pad, wherein the redistributed pressure load is exerted upon the body surrounding the supported region.

One variation of the portable support assembly may generally define a securement area for placement against the region of the body requiring support such as the sacrum. The securement area may generally comprise a central portion with a first conformable portion and/or second conformable portion extending from either side of the central portion. The first and/or second conformable portions may be flexible enough to allow for the portions to be wrapped around or about at least a portion of the patient's body such that the assembly may remain secured to the body even when the patient moves about thereby maintaining the central portion against the supported region of the body.

The central portion may provide the greatest amount of localized support to the patient body by utilizing several fluid layers which are contained one within another to receive the localized loading from the protuberance from the patient's body and distribute the localized load onto the surrounding areas and to further control displacement or inhibit or prevent the bottoming out of the fluid layers. The central portion may thus contain one or more fluid filled individual pods which may be enclosed entirely within an inner fluid pad which envelopes the one or more pods within a secondary layer of fluid. The inner fluid pad may be localized along the central portion. Both the one or more pods and inner fluid pad are then enclosed entirely by a tertiary layer of fluid within an outer fluid pad which may extend over the entire assembly. Each of the fluid layers may be secured to an outer shell which is relatively stiffer than the fluid layers and may restrict or limit the expansion or movement of the fluid pods and/or fluid pads. While the assembly is adjustable to fit a particular patient, the outer pad, in particular, may optionally be filled with the fluid to a variable amount to further ensure that the assembly may be fitted or conformed to the anatomy of a particular patient.

Each of the one or more pods may be separated from one another such that no fluid communication occurs between the pods and/or with the inner pad. Similarly, the inner pad ma be separate from the outer pad such that no fluid communication occurs between the two. In other variations, some fluid communication may occur between the inner pad and outer pad so long as the inner pad constrains and prevents the over-compression of the one or more pods to control their displacement and inhibit their bottoming out.

Each of the pods and/or fluid pads may be filled with an incompressible fluid such as water, viscous oil, or some other biocompatible fluid. Yet in other variations, the pods and/or fluid pads may be filled alternatively with a gas such as air, nitrogen, etc. In yet additional variations, the one or more pods and/or fluid pads may be filled with either a fluid or gas or a combination of both depending upon the desired degree of cushioning and force distribution.

The one or more fluid pods may each occupy an envelope of, e.g., 1 cm×1 cm×0.5 cm to about 3 cm×3 cm×3 cm, in an uncompressed state and they may be formed into various shapes, e.g., spherical, cylindrical, cubical, etc. Moreover, each of the pods may be formed from various materials such as polyurethane, silicone, vinyl, nylon, polyethylene vinyl acetate (PEVA), etc. having a thickness ranging from, e.g., 0.1 mm to 5 mm. Although the figure illustrates four pods, the number of pods contained within the inner pad may range anywhere from, e.g., 1 to 30 or more, arranged either uniformly or arbitrarily within the inner pad. Additionally, while the pods may be unconstrained within the inner pad such that they freely move relative to one another, the pods may be secured within the inner pad either to one another or to the inner pad itself such that their relative movement is constrained.

In yet other variations, rather than utilizing pods having as fluid contained within, one or more spring assemblies may be used to provide the cushioning support. These spring assemblies may utilize various spring types such as leaf or compression springs or various other types of biasing mechanisms.

In either case, the pods may transfer localized loads from the patient received by a few pods either to adjacent pods through the compression and transfer of pressure to adjacent contacting pods or through transmission via the fluid in the inner pad and/or outer pad. The amount of compression of the pods themselves may be controlled by the inner pad which envelopes the pods within a pad localized over the central portion. The inner pad may function as a hammocking layer to constrain the amount of displacement experienced by the individual pods but because the inner pad itself may be fluid filled, the inner pad may further provide support to the patient's body while also restricting compression of the pods. The amount of compression experienced by the individual pods may thus be controlled by the inner pad to range anywhere from, e.g., 0% to 90% or 10% to 90%), of the uncompressed height of the pods.

The inner pad may be sized into various configurations depending upon, the number of pods or the area of the body to be supported. Moreover, the inner pad may also be made from the same or similar material as the pods, e.g., polyurethane, silicone, vinyl, nylon, polyethylene vinyl acetate (PEVA), etc. While the inner pad may be filled with a fluid (or gas or combination of both), as described above, the inner pad may alternatively be devoid of fluid and instead be used to constrain the expansion of the individual pods. Thus, inner pad may be optionally vented to allow for any trapped air to vent from between the pods when the pods undergo compression.

While the one or more pods and inner pad may be concentrated particularly around the region of the body to be supported, an additional outer pad may enclose and surround the inner pad which further encloses the one or more pods. The outer pad may be similarly filled with a fluid or gas (or combination of both), as described above, and may be enclosed by a layer of material either the same or similar to the material of the inner pad and/or pods and further have a uniform or variable thickness ranging from, e.g., 0.5 mm to 4 cm. The outer pad may further constrict the compression of the inner pad which in turn constricts the compression of the one or more pods while additionally providing cushioning support to the surrounding tissue or body structures. Moreover, the outer pad may further extend over the length of the entire assembly to provide cushioning support to the region of the body upon which the assembly is secured.

Further supporting the assembly is the outer shell which may function as a restricting support to control displacement and inhibit the further compression of the outer pad to prevent the patient's body from bottoming out. The outer shell may be formed on a single side of the assembly such that when the assembly is worn by the patient, the outer shell may be positioned away from the skin of the patient such that the outer pad remains in contact with the patient. The outer shell may be accordingly made to be relatively stiffer than the outer pad yet still be flexible enough for conforming over or around the patient's body. Accordingly, the outer shell may be made from materials including plastics such as polypropylene, ABS, PVC, polyethylene, nylon, acrylic, polycarbonate, etc. The outer shell may also be fabricated from other materials such as polymers, carbon fiber, light weight metals, elastomeric materials, rubbers, etc. Depending upon the material used, the outside shell can have a thickness ranging from, e.g., 1 mm to 3 cm.

When the patient wears the support assembly, the one or more fluid filled pods may thus support the body portion (such as the sacrum or trochanter) and due to the weight of the patient, the one or more pods may compress against one another by a limited amount. However, the one or more pods may be inhibited from bottoming out due to the surrounding, hammocking inner pad. The pressure on the body portion may thus be reduced and distributed/transferred to the surrounding fluid present in the inner pad. Moreover, the presence of the surrounding outer pad may further transmit and redistribute the induced pressure upwards towards and against the surrounding body portions, such as the thigh area. This decrease in pressure can lead to a reduction in pressure against the localized body region to a value of less than or approximately 4.3 kPa and hence prevent tissue necrosis and reduce the occurrence of pressure ulcers.

In yet another variation, an assembly may further incorporate additional localized support regions along different portions of the assembly. Other variations of the assembly may incorporate baffles and other mechanisms to optionally create interconnected fluid regions. These regions may allow for reducing the amount of fluid in the entire system and prevent the fluid from pooling in one area.

In yet another variation, open cell foam may be placed between the individual inner and outer fluid layers. This foam layer may be saturated with fluid and allow for the transfer of fluid pressure between the different fluid layers.

Additional variations may incorporate a breathable layer covering at least a portion of the outer pad. The layer may be porous and can be made from materials such as cotton, etc., such that air may circulate through the pores or openings.

In yet other variations, one or more vibrating elements may be attached or integrated into the assembly, e.g., along the outer layer of the outer pad. These vibrating elements may vibrate to impart micro or macro vibrations directly against the contacted skin surface to relieve pressure over the contact area or into the fluid pad itself to indirectly vibrate against the skin surface. The vibrating elements may generate microvibrations on the order of about, e.g., 10 to 500 microns, in amplitude with a frequency ranging from about, e.g., 10 Hz to 300 Hz. These vibrations may allow for increased blood circulation and may also help decrease the incidence of pressure ulcers. Moreover, the vibrating elements may be comprised of piezoelectric, nitinol, or any other actuator driven elements.

In yet other variations, any of the embodiments described herein may incorporate various temperature control mechanisms. These may include one or more regions within the support pad assemblies which may be cooled and/or heated to prevent and/or treat pressure ulcers.

Alternative variations of the outer shell assembly may be utilized with any of the features described herein. One variation may include a support assembly having a central support which incorporates a fabric portion. A first support portion and a corresponding second support portion on an opposite side may each be angularly coupled to central portion and a separate back support portion may also be coupled to the central support.

The central portions as well as support portions and back support portion may be comprised of a conformable material (e.g., malleable metal such as aluminum or plastics, foams, or any other bendable material) which is relative stiffer than the fabric portion and inner or outer pads. The supporting portions may provide adequate support to a patient when the assembly is placed, e.g., upon a mattress or platform, while enabling the assembly to bend or flex into placement against the patient body when the patient lies upon the assembly. The support portions may incorporate a corresponding first conformable portion and second conformable portion fabricated from a stretchable or distendible material such as a mesh or fabric which is supported by one or more adjustable straps (e.g., straps with hook-and-loop fastening portions) coupling the conformable portions to their respective support portions. The flexibility of the conformable portions may enable the shell assembly to shape or conform more closely to the patient body and may also provide for enhanced comfort.

In another variation, the support portions may be attached to the central portion via one or more adjustable cords (e.g., bungee cords) columns pivotably attached to a platform and extending, into connection with one or more openings within the respective support portions. In yet other variations, the supporting side portions may be comprised of composite assemblies which are adjustably configurable. The composite assembly may generally include a number of individual support elements (e.g., plastic, metal, foam, etc.) which are connected to one another along respective longitudinal axes in an alternating pattern. A tensioning member such as a wire, screw, etc., may be passed through each end of the support elements along, the longitudinal axes with a tightening member coupled at the ends of the tensioning member.

In yet another outer shell assembly, the support portions may be comprised of angled supports which are adjustably secured to respective first and second adjustable supports which may be rotatable about first and second pivots. The adjustable supports may each support respective first and second conformable portions which provide a surface for supporting the bladder assembly against the patient.

In yet another variation of the outer shell assembly, the conforming supports may extend in a curved or arcuate manner from the central support portion in a shaped shell configuration. The conforming supports may extend in strips or members which are shaped, e.g., like flower petals, and the supports may be secured in place using any number of securement mechanisms, e.g., friction hinge mechanisms, electromechanical locking systems, hydraulic locking systems, magnetic locking systems, electro or magnetoreological locking systems, etc.

Additionally and/or optionally, any of the outer shell assemblies may incorporate one or more zones throughout various regions of the shell which may selectively or simultaneously squeeze, vibrate, or otherwise actuate. These selective zones may vibrate at a selected frequency and/or amplitude and may be actuated at fixed intervals or times.

Yet another variation of the outer shell assembly may include conforming supports which extend in a curved or arcuate shape for conforming more closely against the patient's body. The supports may each integrate one or more support members which are adjacent to respective sliding supports which may be tuned to push in or out relative to the central support portion to adjust a rotation or bend radius of each support independently of one another or simultaneously with each support. By moving or conforming the support portions against the patient's body, the fluid within the pad may be redistributed to reduce an pressure that may result below any bony prominences of the patient body.

With any of the variations described herein, different features and aspects from each of the variations may be combined with one another in various combinations.

BRIEF DESCRIPTION OF THE DRAWINGS

FIG. 16 shows a perspective view of another variation of an outer shell assembly where the support portions may be secured with one or more adjustable cords.

FIGS. 17A to 17C show front and perspective views of yet another variation of the supporting shell assembly utilizing, columns for adjustably supporting the support portions.

DETAILED DESCRIPTION OF THE INVENTION

Figure 1A:
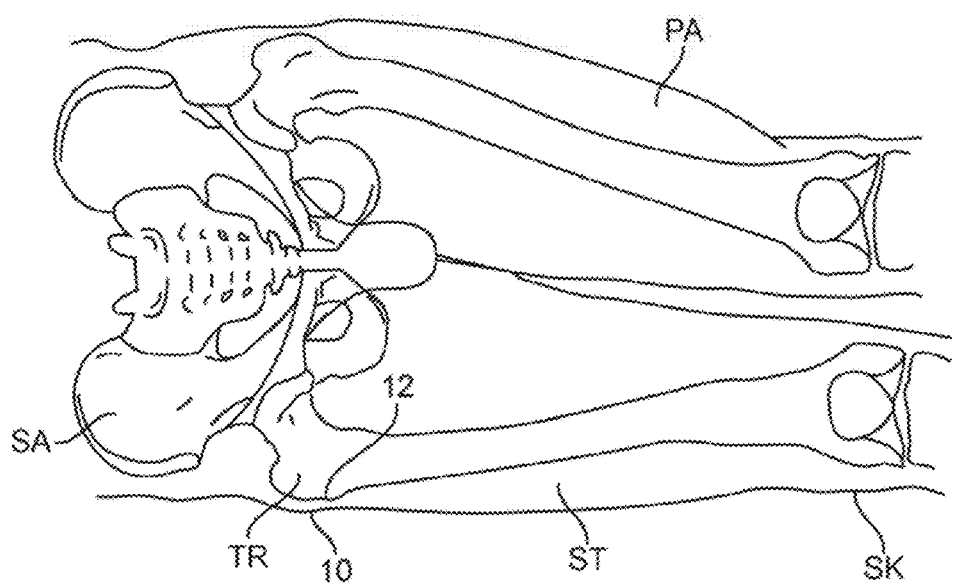
FIG. 1A shows a portion of a patient's body and the resultant induced pressure imparted on portions of the body such as the trochanter.
Figure 1B:
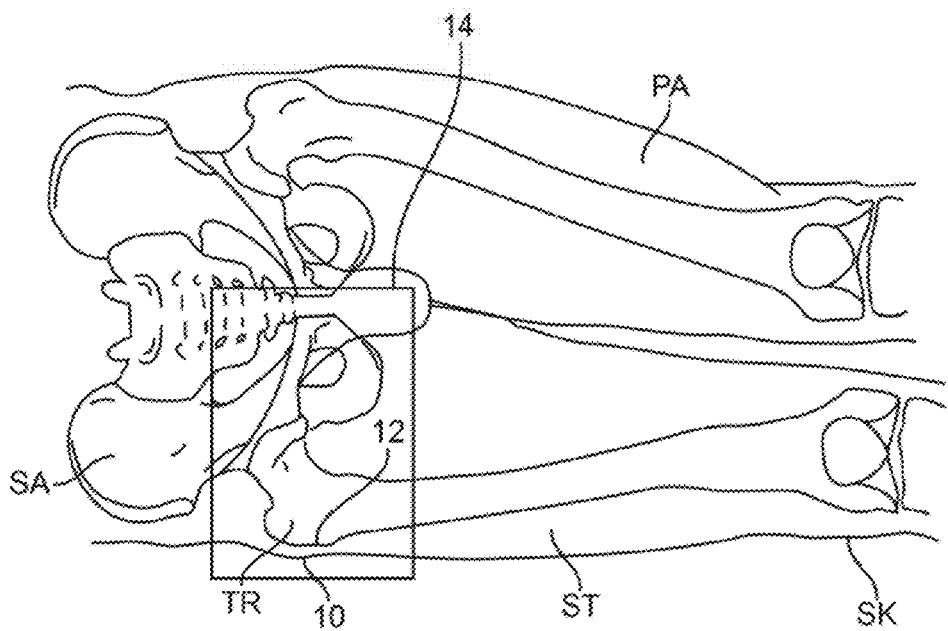
FIG. 1B shows a portion of the patient's body with a portable support assembly worn upon the body, e.g., around the hips, to alleviate pressure.

Generally, in a healthy individual, the presence of muscle mass and soft tissue ST usually functions to distribute and relieve pressure from bony protuberances of the body contacted against the underlying surface. However, when a patient PA is forced to lie on one portion of their body for extended periods of time, areas such as the sacrum SA or trochanter TR may compress a region of the skin SK and tissue 12 between the protuberance and a contact region 10 formed against the underlying surface, as shown in FIG. 1A.

Typical pressures generated in the hip area for healthy individuals lying against a surface may range around 4 kPa. However, for older and/or diseased individuals, the contact pressures between regions of bony prominence and the skin is generally higher due to various factors such as muscle atrophy. For instance, increased pressures were found to range around 7.3 kPa. Blood circulation become restricted and tissue necrosis typically begins when pressures range above 4.3 kPa leading to the development of pressure ulcers.

Figure 18:
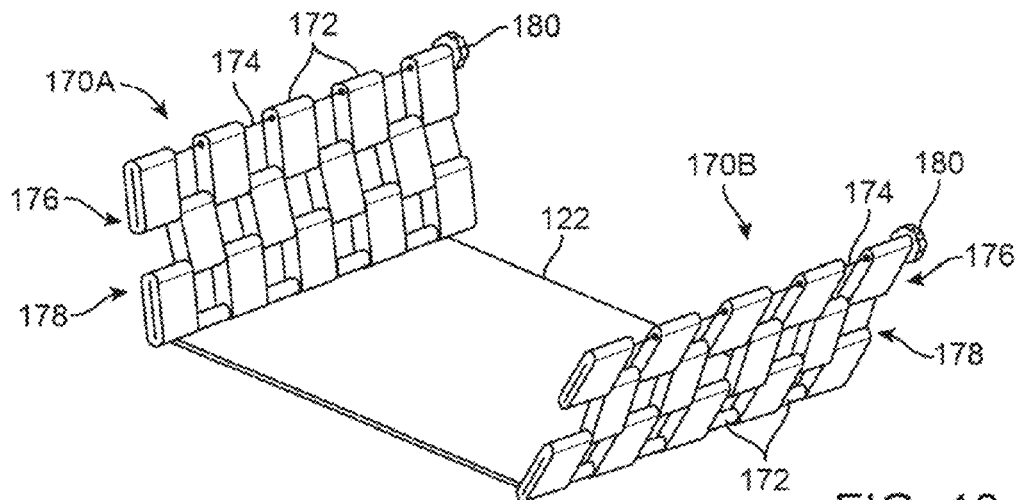
FIG. 18 shows a perspective view of yet another variation where the central portion ma incorporate respective composite assemblies which are adjustably configurable.

Generally, a portable support assembly 14 may be worn by an individual who may be bed-stricken for an extended period of time to prevent the formation of pressure ulcers. Such a portable support assembly 14 may be worn by the individual around particular regions of the body where pressure ulcers tend to form, e.g., sacrum SA, trochanter TR, ischium, as well as any other region of the body where support is desired. The portable support assembly 14 may be formed into an elongated shape to be wrapped entirely around the patient's body, e.g., around the hips or lower back, or a portion of the body, e.g. around the ankles or feet. Thus, although the example shown in FIG. 18 illustrates the assembly 14 placed around the trochanter TR or sacrum SA, other embodiments may include various shapes of the assembly 14 which may be sized for particular body regions and are intended to be within the scope of this disclosure.

Moreover, the support assembly 14 is configured to be portable such that it may be worn directly over or upon the patient's body independently from the underlying, bed or cushion. Accordingly, the patient may utilize the support assembly 14 on any underlying bed or platform. Additionally, while the examples described illustrate portable support assemblies, the support assembly may be integrated into a bed, underlying cushion, and/or mattress pad if so desired.

Figure 2:
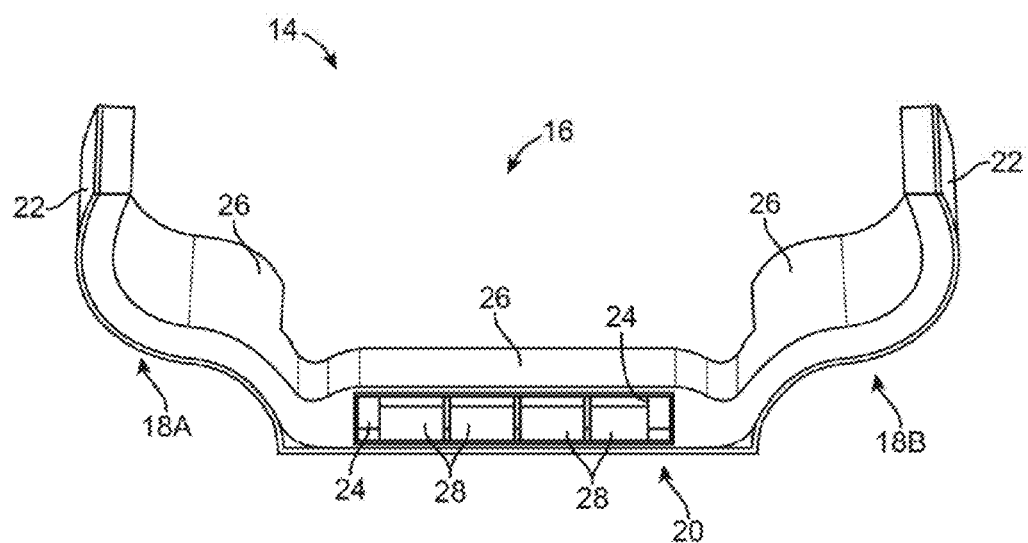
FIG. 2 shows a cross-sectional end view of one variation of a portable support assembly illustrating the various layered fluid pads contained within.

One variation of the portable support assembly 14 is illustrated in the cross-sectional view of FIG. 2, which illustrates a wearable hip-support system. In this variation, the support assembly 14 may generally define a securement area 16 for placement against the region of the body requiring support such as the sacrum SA. The securement area 16 may generally comprise a central portion 20 with first conformable portion 18A and/or second conformable portion 188 extending from either side of the central portion 20. The first and/or second conformable portions 18A, 18B may be flexible enough to allow for the portions 18A, 188 to be wrapped around or about at least a portion of the patient's body such that the assembly 14 may remain secured to the body even when the patient moves about thereby maintaining, the central portion 20 against the supported region of the body.

The central portion 20 may provide the greatest amount of localized support to the patient body by utilizing several fluid layers which are contained one within another to receive the localized loading from the protuberance from the patient's body and distribute the localized load onto the surrounding areas and to further control their displacement and inhibit or prevent the bottoming out of the fluid layers. The central portion 20 may thus contain one or more fluid filled individual pods 28 which may be enclosed entirely within an inner pad 24 which envelopes the one or more pods 28 within a secondary layer of fluid. The inner pad 24 may be localized along the central portion 20. The inner pad 24 may be filled with a fluid (or gas) or optionally be devoid of any fluid, as described in further detail below. Both the one or more pods 28 and inner pad 24 are then enclosed entirely by a tertiary layer of fluid within an outer pad 26 which may extend over the entire assembly 14. Each of the fluid layers may be secured to an outer shell 22 which is relatively stiffer than the fluid layers and may restrict or limit the expansion or movement of the fluid pods 28 and/or pads 24, 26. While the assembly 14 is adjustable to fit a particular patient, the outer pad 26, in particular, may optionally be filled with the fluid to a variable amount to further ensure that the assembly 14 may be fitted or conformed to the anatomy of a particular patient.

Each of the one or more pods 28 may be separated from one another such that no fluid communication occurs between the pods 28 and/or with the inner pad 24. Similarly, the inner pad 24 may be separate from the outer pad 26 such that no fluid communication occurs between the two. In other variations, some fluid communication may occur between the inner pad 24 and outer pad 26 so long as the inner pad 24 constrains and prevents the over-compression of the one or more pods 28 to control their displacement and inhibit their bottoming out.

Each of the pods 28 and/or fluid pads 24, 26 may be filled with an incompressible fluid such as water, salt solution, viscous oil, or some other biocompatible fluid. Yet in other variations, the pods 28 and/of fluid pads 24, 26 may be filled alternatively with a gas such as air, nitrogen, etc. In yet additional variations, the one or more pods 28 and/or fluid pads 24, 26 may be filled with either a fluid or gas or a combination of both depending upon the desired degree of cushioning and force distribution.

The one or more fluid pods 28 may each occupy an envelope of, e.g., 1 cm×cm×0.5 cm to about 3 cm×3 cm×3 cm in an uncompressed state and they may be formed into various shapes, e.g., spherical, cylindrical, cubical, etc. Moreover, each of the pods may be formed from various materials such as polyurethane, silicone, vinyl, nylon, polyethylene vinyl acetate (PEVA), etc. having a thickness ranging from, e.g. 0.1 mm to 5 mm. Although the figure illustrates four pods 28, the number of pods 28 contained within the inner pad 24 may range anywhere from e.g., 1 to 30 or more, arranged either uniformly or arbitrarily within the inner pad 24. Additionally, while the pods 28 may be unconstrained within the inner pad 24 such that they freely move relative to one another, the pods 28 may be secured within the inner pad 24 either to one another or to the inner pad 24 itself such that their relative movement is constrained.

In either case, the pods 28 may transfer localized loads from the patient received by a few pods 28 either to adjacent pods through the compression and transfer of pressure to adjacent contacting pods or through transmission via the fluid in the inner pad 24 and/or outer pad 26. The amount of compression of the pods 28 themselves may be controlled by the inner pad 24 which envelopes the pods 28 within a pad localized over the central portion 20. The inner pad 24 may function as a hammocking layer to constrain the amount of displacement experienced by the individual pods 28 but because the inner pad 24 itself may be fluid filled, the inner pad 24 may further provide support to the patient's body while also restricting compression of the pods 28. The amount of compression experienced by the individual pods 28 may thus be controlled by the inner pad 24 to range anywhere from, e.g., 0% to 90% (or 10% to 90%), of the uncompressed height of the pods 28. For example, for a pod 28 having an uncompressed height of 3 cm, the compression of the pod 28 may range anywhere from, e.g., 0 cm to 2.7 cm.

The inner pad 24 may be sized into various configurations depending upon, e.g., the number of pods 28 or the area of the body to be supported. Moreover, the inner pad 24 may also be made from the same or similar material as the pods 28, e.g., polyurethane, silicone, vinyl, nylon, polyethylene vinyl acetate (PEVA), etc. While the inner pad 24 may be filled with a fluid (or gas or combination of both), as described above, the inner pad 24 may alternatively be devoid of fluid and instead be used to constrain the expansion of the individual pods 28. Thus, inner pad 24 may be optionally vented, to allow for any trapped air to vent from between the pods 28 when the pods 28 undergo compression.

While the one or more pods 28 and inner pad 24 may be concentrated particularly around the region of the body to be supported, an additional outer pad 26 may enclose and surround the inner pad 24 which further encloses the one or more pods 28. The outer pad 26 may be similarly filled with a fluid or gas (or combination of both), as described above, and may be enclosed by a layer of material either the same or similar to the material of the inner pad 24 and/or pods 28 and further have a uniform or variable thickness ranging from, e.g., 0.5 mm to 4 cm. The outer pad 26 may further constrict the compression of the inner pad 24 which in turn constricts the compression of the one or more pods 28 while additionally providing cushioning support to the surrounding tissue or body structures. Moreover, the outer pad 26 may further extend over the length of the entire assembly 14 to provide cushioning support to the region of the body upon which the assembly 14 is secured.

Additionally, while the outer pad 26 may have a thickness ranging anywhere from, e.g., 5 mm to 2 cm or more (such as in areas in contact against the sacrum), the inner pad 24, outer pad 26, and/or pods 28 may be filled with a fluid having a density which is relatively higher than the density of a body. For example, the density of the human body is about 1.01 $g/cm^2$ and a salt solution filled within any of the pads 24, 26 and/or pods 28 can have density of, e.g., 1.03 to 1.1 $g/cm^2$. By using a highly saturated salt solution used as the fluid, a further cushioning effect may be achieved for providing comfort to the patient when the assembly is in use.

Further supporting the assembly is the outer shell 22 which may function as a restricting support to control displacement and inhibit the further compression of the outer pad 26 to prevent the patient's body from bottoming out. The outer shell 22 may be formed on a single side of the assembly 14 such that when the assembly 14 is worn by the patient, the outer shell 22 may be positioned away from the skin of the patient such that the outer pad 26 remains in contact with the patient. The outer shell 22 may be accordingly made to be relatively stiffer than the outer pad 26 yet still be flexible enough for conforming over or around the patient's body. Accordingly, the outer shell 22 may be made from materials including plastics such as polypropylene, ABS, PVC, polyethylene, nylon, acrylic, polycarbonate, etc. The outer shell 22 may also be fabricated from other materials such as polymers, carbon fiber, light weight metals etc. Depending upon the material used, the outside shell 22 can have a thickness ranging from, e.g., 1 mm to 3 cm.

When the patient wears the support assembly, the one or more fluid filled pods 28 may thus support the body portion (such as the sacrum SA or trochanter TR) and due to the weight of the patient, the one or more pods 28 may compress against one another by a limited amount. However, the one or more pods 28 may be inhibited from bottoming out due to the surrounding hammocking inner pad 24. The pressure on the body portion may thus be reduced and distributed/transferred to the surrounding fluid present in the inner pad 24. Moreover, the presence of the surrounding outer pad 26 may further transmit and redistribute the induced pressure upwards towards and against the surrounding body portions, such as the thigh area. This decrease in pressure can lead to a reduction in pressure against the localized body region to a value of less than or approximately 4.3 kPa and hence prevent tissue necrosis and reduce the occurrence of pressure ulcers.

In another variation, the one or more pods 28 may be connected directly to the outer shell 22 and contained by the hammocking inner pad layer 24 which prevents the pods 28 from bottoming out, as described, above. The outer fluid pad 26 may be laid atop the one or more pods 28 and hammocking inner layer 24. Alternatively, the one or more pods 28 (contained within the hammocking inner layer 24) may come into direct contact against the patient and the outer fluid pad 26 may instead be attached directly to the outer shell 22.

Figure 3:
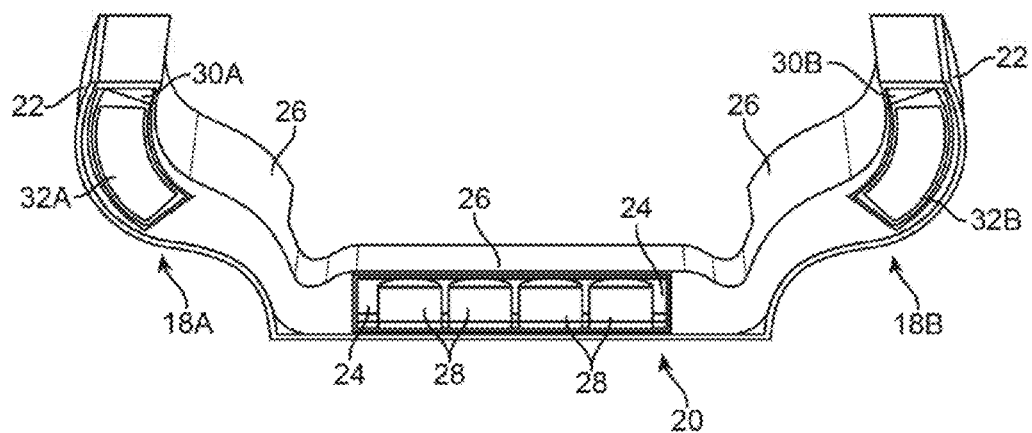
FIG. 3 shows a cross-sectional end view of another variation of the support assembly illustrating additional fluid pads contained within.

In yet another variation. FIG. 3 shows a cross-sectional view of an assembly which is similarly constructed to the variation of FIG. 2 but which may further incorporate additional localized support regions. For instance, in the variation shown, a first fluid inner pad 30A having one or more pods 32A contained within may be integrated along the first conformable portion 18A extending from the central portion 20. Similarly, a second fluid inner pad 30B having one or more pods 328 contained within may be integrated along the second conformable portion 1813 extending from the opposite side of the central portion 20. In this variation, the conformable portions 18A, 1813 may be wrapped or secured against the hips of the patient such that the corresponding inner pads 30A, 308 are positioned over either or both trochanters TR of the patient while the central portion 20 is positioned over the sacrum SA to provide support around the entire hip and lower back regions of the patient. As described herein, the number and size of the pods 32A, 3213 may be varied.

Figure 4A:
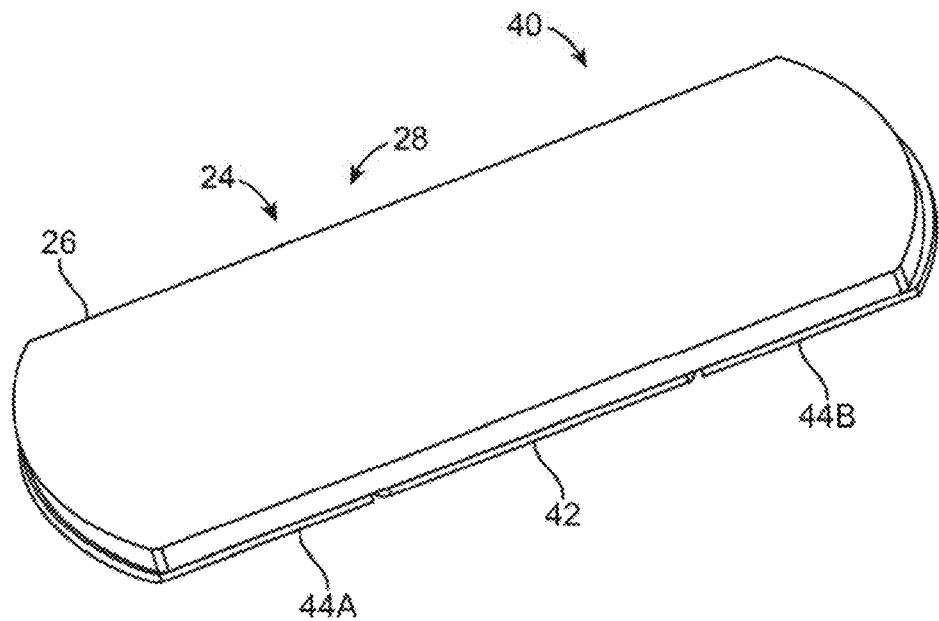
FIGS. 4A and 4B show perspective views of another variation of the support assembly which may be layered upon a hinged platform.
Figure 4B:
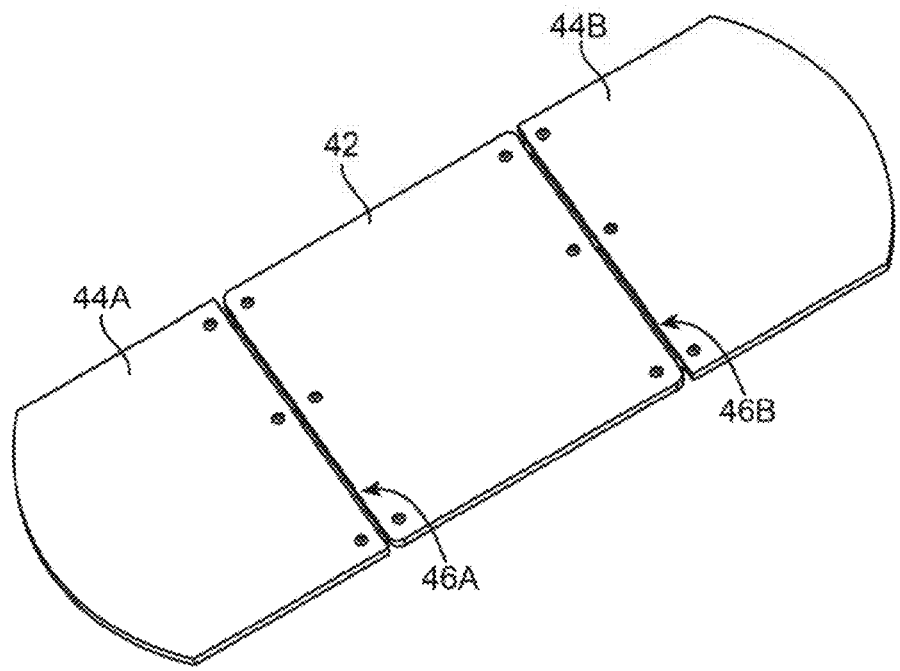

While the support assembly 14 may be sized in various configurations depending upon the region of the body to which the assembly is to be positioned, another example of an assembly configuration is shown in the perspective views of FIGS. 4A and 4B. In this example, the support system may be configured as a hinged fluid pad assembly 40 having a central portion 42 and a first foldable portion 44A and a second foldable portion 44B extending from either side of the central portion 42. The outer shell of the foldable portions 44A, 44B may be coupled via corresponding first hinged region 46A and second hinged region 4613 such that the assembly 40 may be laid flat upon a bed or platform. The inner fluid pad 24 and one or more pods 28 may be positioned upon the central portion 42 and/or optionally along the first and/or second foldable portions 44A, 44B as well while the outer pad 26 may extend continuously along the length of the entire assembly 40. In use, the assembly 40 may be laid flat and folded over upon or against the patient's body and secured accordingly.

Other variations of the assembly may incorporate baffles and other mechanisms to optionally create interconnected fluid regions. These regions may allow for reducing the amount of fluid in the entire system and prevent the fluid from pooling in one area.

In yet another variation, open cell foam may be placed between the individual inner and outer fluid layers. This foam layer may be saturated with fluid and allow for the transfer of fluid pressure between the different fluid layers.

Figure 5:
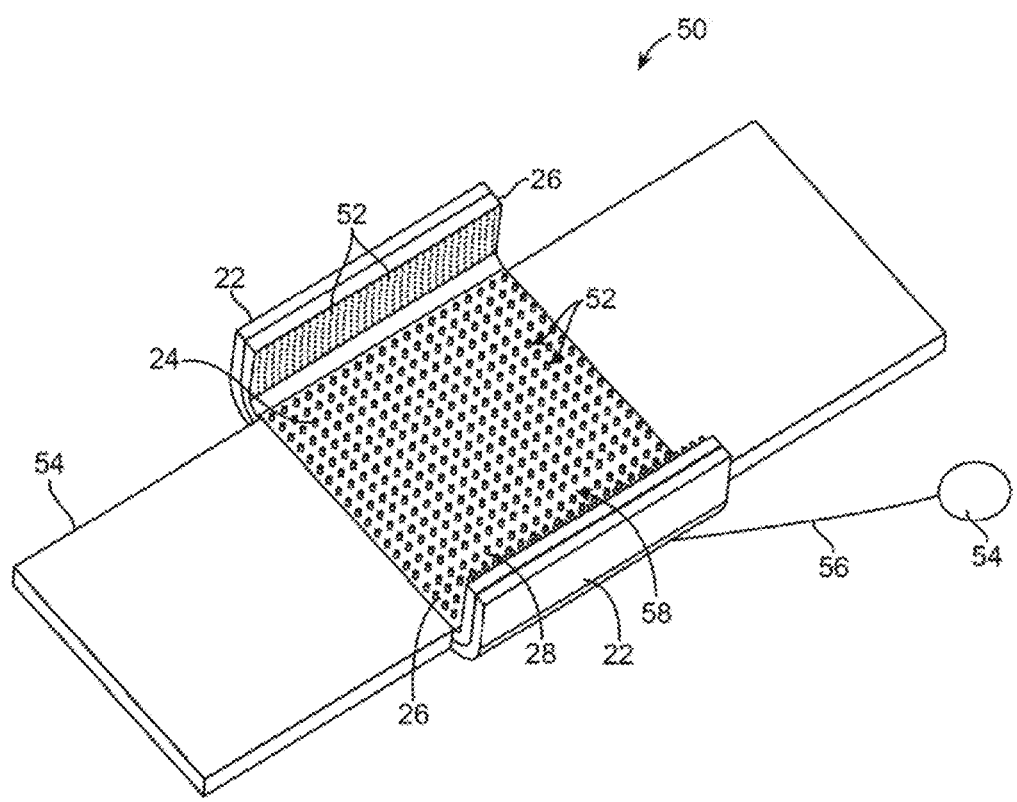
FIG. 5 shows a perspective view of yet another variation of the support assembly incorporating features such as a cooling mechanism and/or a plurality of vibrating elements.

FIG. 5 shows a perspective view of yet another variation in which the support assembly 50 may incorporate a breathable layer covering at least a portion of the outer pad 26. The layer may be porous and can be made from materials such as cotton, etc., such that air may circulate through the pores or openings 52. A pump 54 coupled via a fluid line 56 may be optionally attached to the assembly 50 to pump air through the pores or openings 52.

In yet other variations, one or more vibrating elements 58 may be attached or integrated into the assembly 50, e.g., along the outer layer of the outer pad 26. These vibrating elements 58 may vibrate to impart micro or macro vibrations directly against the contacted skin surface to relieve pressure over the contact area or into the fluid pad itself to indirectly vibrate against the skin surface. The vibrating elements 58 may generate micro-vibrations on the order of about, e.g., 10 to 500 microns, in amplitude with a frequency ranging from about, e.g., 10 Hz to 300 Hz. These vibrations may allow for increased blood circulation and may also help decrease the incidence of pressure ulcers. Moreover, the vibrating elements 58 may be comprised of piezoelectric, nitinol, or any other actuator driven elements.

In other variations, the assembly 50 may be integrated with an optional mattress topper 54 to provide stability to the assembly 50 when positioned against the patient.

Figure 6A:
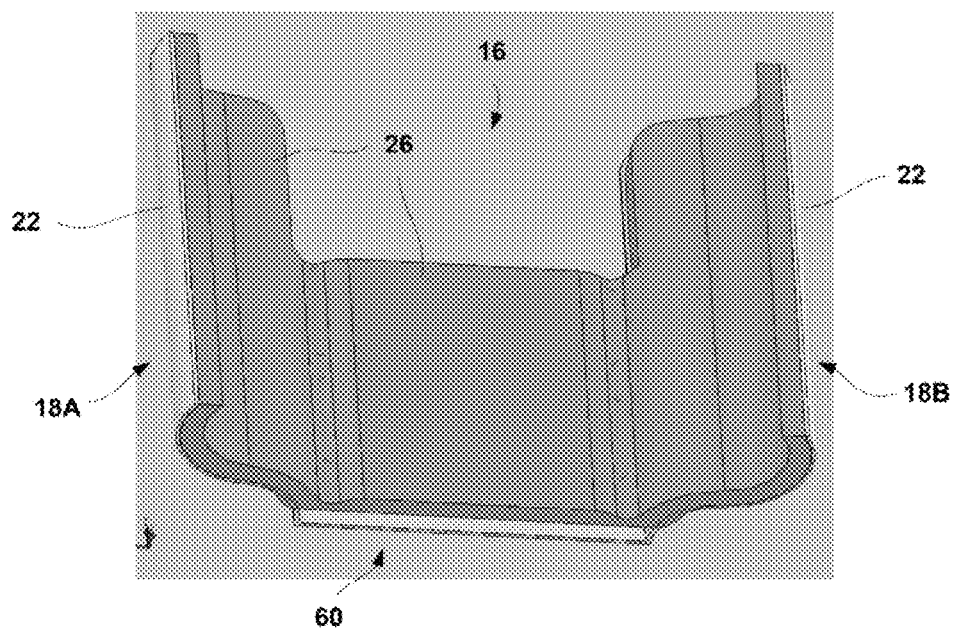
FIGS. 6A and 6B show perspective and side views of another variation of the support assembly which utilizes one or more spring assemblies in combination with the inner and/or outer pad.
Figure 6B:
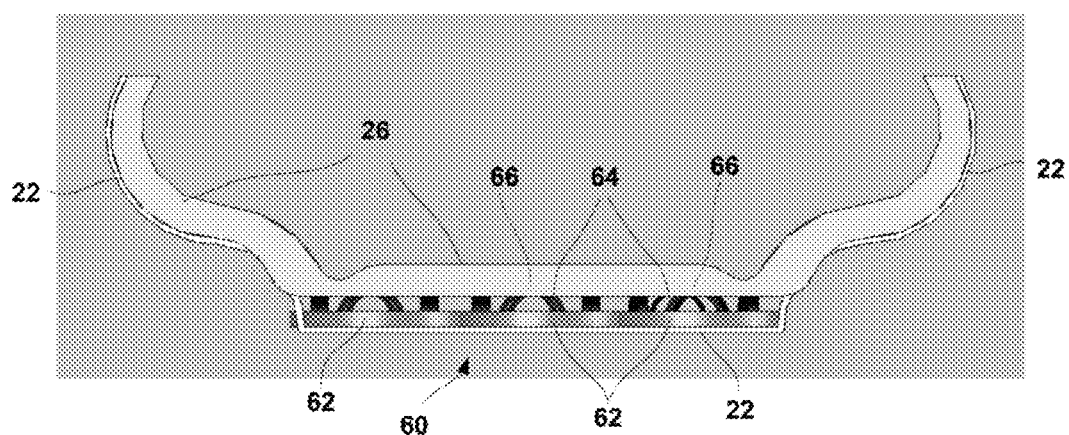

In yet another variation, the support assembly may utilize one or more spring, assemblies in combination with the inner pad 24 and/or outer pad 26 rather than using the one or more pods 28. An example is shown in the perspective view of FIG. 6A which shows a variation of the assembly with outer pad 26 positioned atop one or more spring assemblies 60 rather than one or more pods. FIG. 6B shows a partial cross-sectional side view of one or more spring assemblies 60 secured upon the outer shell 22 and the outer pad 26 positioned atop the spring assemblies 60. The number of individual compression assemblies 60 in the array can vary, e.g., from 1 to 25 or more depending upon the desired treatment area. Moreover, each of the individual spring assemblies 60 is designed to be non-bottoming and further designed to reduce the pressure to less than or equal to, e.g., 32 mm of Hg, when a person uses the system.

One variation of a spring assembly may have an individual base 62 for securement to the outer shell 22 and a corresponding top layer 66 for contacting against the outer pad 26 and/or directly against the patient body. Between the top layer 66 and base 62 are one or more biasing members 64 e.g. spring elements. An example is shown in the perspective view of FIG. 7 which illustrates the top layer 66 and base 62 formed in a circular configuration although they may be formed in any number of shapes which are suitable for placement between the shell 22 and outer pad 26. The variation of biasing members 64 shown may comprise superelastic shape memory alloys such as heat-formed Nitinol formed, e.g., into flattened strips of material which are configured into leaf or compression springs, as shown. When a force is applied to the top layer 66, such as by the patient body, the biasing members 64 compress and their height decreases in response to the application of the force causing the top layer 66 to move towards the base 62.

Figure 7:
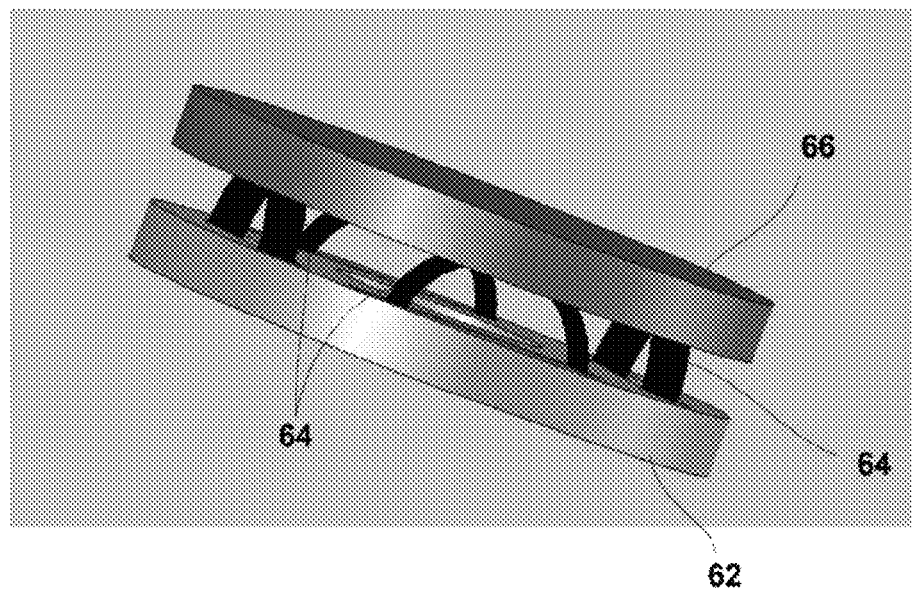
FIG. 7 shows a perspective view of one variation of a spring assembly.

The spring, assembly shown in FIG. 7 is illustrated as having four biasing members 64 but the assembly can have one, two, three, or more biasing members 64. The biasing members 64 can also be made from other materials such as stainless steels, plastics, elastomers, and other suitable materials.

Figure 8:
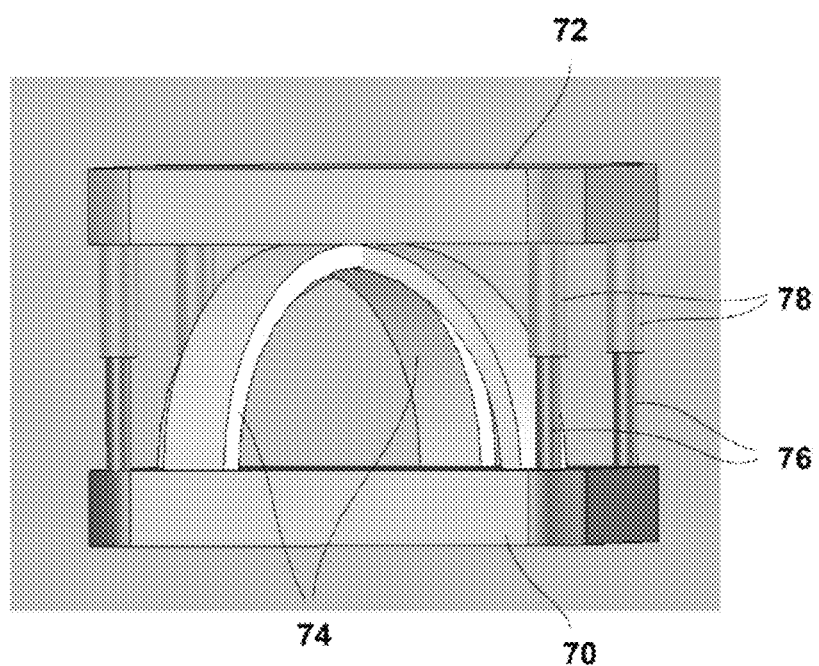
FIG. 8 shows a perspective view of another variation of a spring assembly.

FIG. 8 shows an alternative variation of a spring assembly having a base 70 and a top layer 72 with the biasing members 74 as previously described. The assembly may further have one or more post members 76 extending from the base 70 for translational engagement with one or more corresponding guide members 78 which may be aligned to receive the post members 76. The post members 76 may prevent the top layer 72 from rotating out of alignment with respect to base 70 during use. Moreover, the biasing members 74 may be designed to be a multiple prong anchor or flower design although an of the spring designs described herein may be used.

The individual spring assembly can have a surface area, e.g., from 0.5 to 1.0 $cm^2$ or even up to 200 $cm^2$, and an uncompressed height ranging from, e.g. 1 cm to 3 cm. The biasing members 64 can also vary from having a constant force to having compression systems with a single spring constant or multiple spring constants.

Moreover, various other biasing elements such as extension springs, leaf springs, torsion springs, or any formed or shaped design which can accomplish similar functions may be used. Aside from the design, the different kinds of springs and compression pods may be designed to have spring constants either independently or on a system level such that the displacement or travel to support the patient does not result in pressures greater than, e.g., 4.3 kPA or similar pressures, which can cause tissue necrosis and lead to formation of pressure ulcers.

Figure 9A:
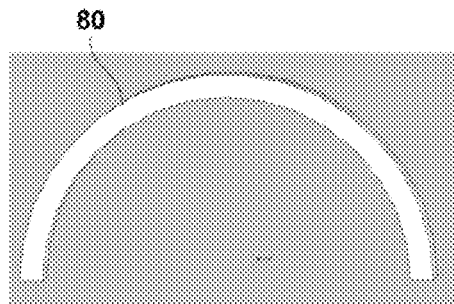
FIGS. 9A to 9D show various spring designs which may be used with any of the spring assemblies.
Figure 9B:
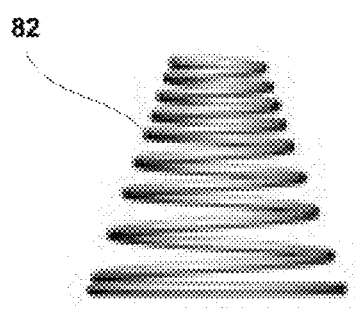
Figure 9C:
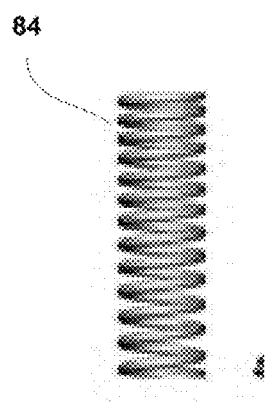
Figure 9D:
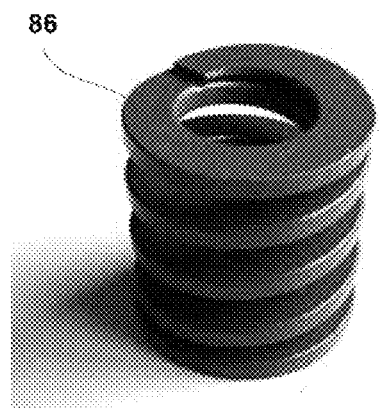

Other examples of various spring designs which may be used with any of the assemblies described herein are shown in FIGS. 9A to 9D. For instance, FIG. 9A shows a side view of a leaf spring 80 while FIGS. 9B and 9C show side views of a conical spring 82 and a cylindrical spring 84, respectively, which may be used as well. FIG. 9D shows a perspective view of an elastomeric spring 86 which may also be used, if so desired.

Experiments

Tests using exemplary embodiments of the support assembly described herein have been conducted utilizing an array of individual fluid pods enclosed within an inner enveloping pad. This assembly was then enveloped within an outer fluid pad where both the fluid pods and outer pads were filled with water. The assembly was positioned near a simulated sacrum region and a similar arrangement was positioned near a simulated trocanter region.

An artificial male hip model was used to which a 0 to 20 lb FLEXIFORCE® (Tekscan, Inc., MA) sensor was attached to the sacrum region of the hip model. The FLEXIFORCE® sensor was used to sense contact force/pressure and an 8 lb load (ball) was used as the simulated load of a patient.

A first test had the hip model placed on a simulated mattress having a foam pillow with a thickness of about 1 cm. The hip model was then loaded three times with the 8 lb load and a corresponding three reading was recorded. A second test was then conducted where the hip model was placed on the support assembly pad and was then loaded with the 8 lb load. The hip model was then loaded again three times with the 8 lb load and a corresponding force reading was recorded. The tabulated results are shown in the following Table 1:

TABLE 1

Force measurements results from simulated loading.

| Test No | Force in N (simulated mattress) | Force in N (support assembly pad) | Force/Pressure (decrease by support assembly pad) |
|---------|---------------------------------|-----------------------------------|---------------------------------------------------|
| 1 | 7.70 | 4.29 | 44% |
| 2 | 6.33 | 3.42 | 46% |
| 3 | 5.65 | 3.42 | 39% |

Accordingly, use of the support assembly pad yielded an average reduction of 43% in measured pressure as experienced by the sacrum.

In another test, another exemplary embodiment of the support assembly (such as the variation shown in FIG. 15A) was tested on a mannequin positioned within the support assembly. The mannequin was further weighed down to increase the amount of weight placed against the support assembly. A measurement of the weighted mannequin was also observed upon a standard mattress without the support assembly for comparison purposes. Pressure sensors were used to record the resulting peak pressure measurements upon the mattress and upon the support assembly as well. Additionally, the overall area of contact between the mannequin and the mattress and between the support assembly was also recorded via a pressure map.

The results were recorded and the change in pressure (as well as contact sensing area) between the mattress and the support assembly were tabulated, as shown in the following Table 2:

TABLE 2

Pressure measurement results from simulated loading upon mannequin.

| Test | Peak Pressure (mmHg) | Sensing Area (in²) |
|------|----------------------|--------------------|
| Mattress | >200 | 41.81 |
| Support Assembly | 63.47 | 135.59 |
| Change | >−68% | 224% |

As observed, the recorded peak pressure values upon the mannequin when placed upon the mattress and compared to when placed upon the support assembly resulted in a pressure reduction of over 68% with an increase in the supporting, area of 224%.

The test was then reproduced upon a human subject and the same measurements were taken, as shown in the following Table 3:

TABLE 3

Pressure measurement results from simulated loading upon human subject.

| Test | Peak Pressure (mmHg) | Sensing Area (in²) |
|------|----------------------|--------------------|
| Mattress | 101.15 | 181.92 |
| Support Assembly | 63.77 | 249.35 |
| Change | −37% | 37% |

As observed, the recorded peak pressure values upon the human subject when placed upon the mattress and compared to when placed upon the support assembly likewise resulted in a pressure reduction of over 37% with an increase in the supporting area of 37%.

Temperature Control

Additionally and/or alternatively, any of the variations described herein may also incorporate the use of temperature modulation and control to further help prevent the formation of pressure ulcers. For example, the support assembly pad may be controlled to have a temperature which is lower than body temperature to help prevent the formation of pressure ulcers while having an assembly pad controlled to have a temperature which is higher than body temperature can be used to treat pressure ulcers which have already formed upon the body. For example, the assembly pad can be configured to control the contacted skin/tissue temperature to within ±10° C. of body temperature.

Figure 10:
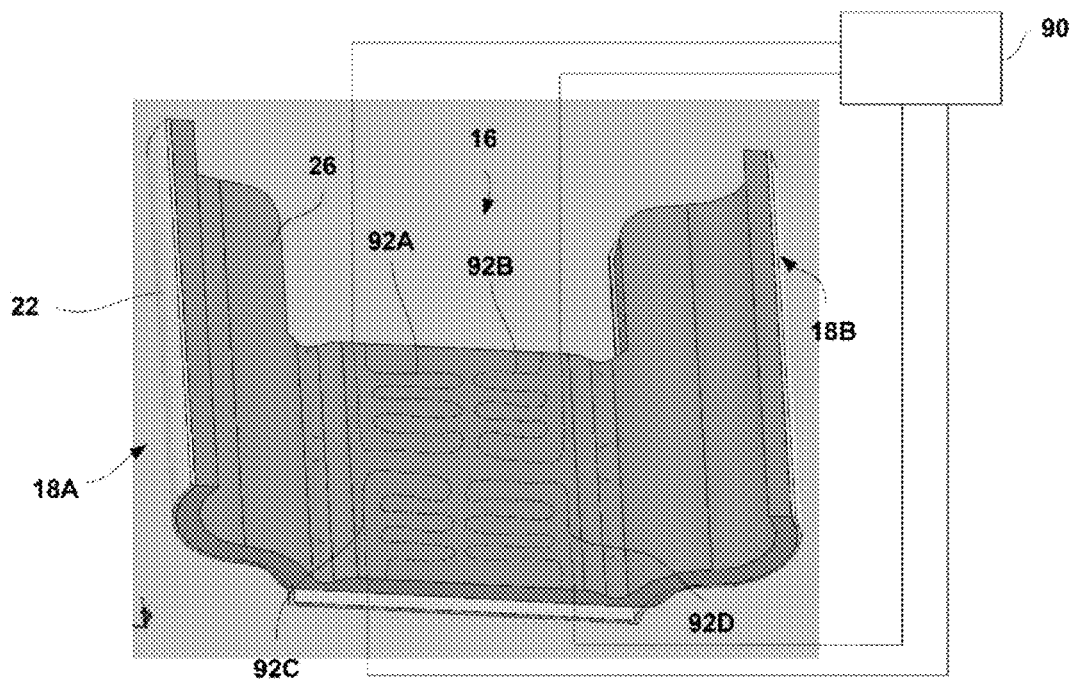
FIG. 10 shows a perspective view of another variation of the support pad assembly having one or more temperature control regions.
Figure 11:
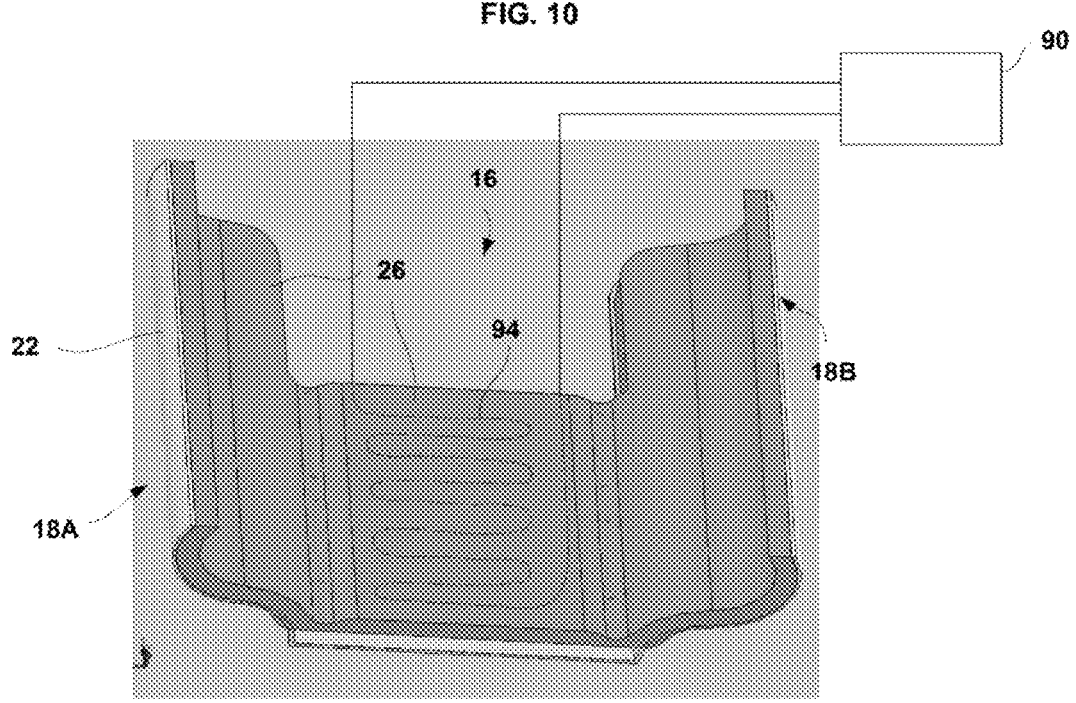
FIG. 11 shows a perspective view of another variation of the support pad assembly having a single temperature control region.

In addition to unidirectional temperature control (either heating or cooling) bidirectional temperature control can be achieved (selectively or alternatively heating and/or cooling). This allows the same assembly pad to be used for prevention and treatment of pressure ulcers. Temperature control can be achieved using any of several various methods and mechanisms. One example is shown in the perspective view of FIG. 10 which illustrates an assembly pad having several individual temperature regions 92A, 92B, 92C, 92I) which may be controlled individually or simultaneously to heat or cool specified regions of the pad assembly. Each of the temperature regions may be in electrical communication with a controller 90, e.g., processor, which may be integrated with the pad assembly or arranged as a separate mechanism. FIG. 11 shows another variation where single temperature region 94 may be integrated over the pad assembly to heat or cool the entire pad assembly in contact with the patient.

The unidirectional or bidirectional temperature control may utilize any number of temperature altering, mechanisms. For example, thermoelectric cooling and heating elements (e.g., Peltier junctions) may be used or resistive heating and cooling elements may be used. Alternatively, inductive heating and cooling elements may also be used. Additionally and/or alternatively, chemically cooling and/or heating reacting materials (e.g., exothermic and/or endothermic) may be used as the fluid filling the one or more pods and/or pads. In yet another alternative, a cooling or heating fluid may be pumped in a circulating manner with an externally located cooling; and/or heating mechanisms in fluid communication with a pumping mechanism.

Figure 12:
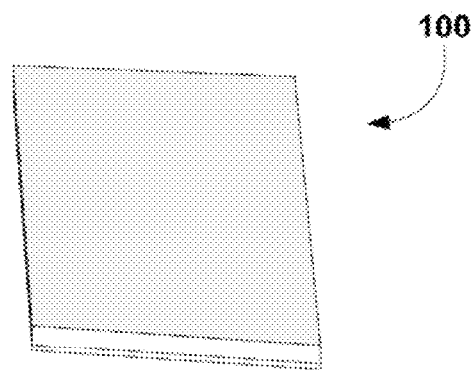
FIG. 12 shows a perspective view of another variation of a support pad configured for alternative uses such as with a wheelchair.
Figure 13:
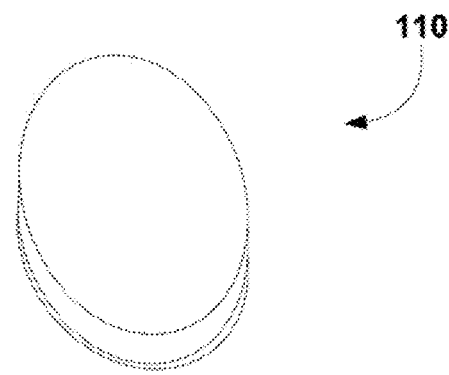
FIG. 13 shows a perspective view of yet another variation of a support pad configured for other regions of the body such as an elbow.

In yet other variations, the pad assembly may be designed for alternative uses. For example, the pad may be configured for use by a patient sitting in a wheelchair, standard chair, or other sitting, standing, or sleeping devices or platforms. An example of a simplified pad assembly 100 is shown in the perspective view of FIG. 12. Alternatively, a pad assembly 110 shown in FIG. 13 may be configured for resting, e.g., during surgery, beneath an extremity such as an elbow or any other portion of the body which may come into contact against a hard surface for an extended period of time. The configured pad 110 may cushion, e.g., the ulnar nerve and may include a flat pad with a single fluid pod, for instance.

Figure 14:
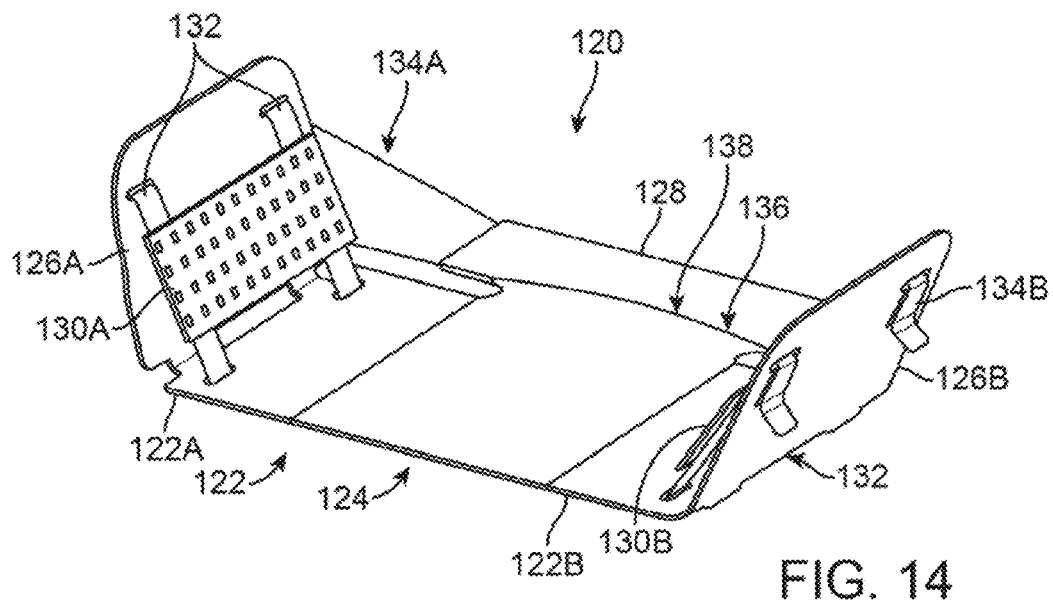
FIG. 14 shows a perspective view of another variation of an outer shell assembly which may incorporate fabric portions and an angled back support.

Yet another alternative of the pad assembly is shown in the perspective view of FIG. 14. In this variation, a support assembly 120 which is designed to confine and conform a fluid bladder to the anatomical features of the patient body (such as hip region, sacrum region etc.) is shown. The support assembly 120 may generally comprise a central support 122 having a first central portion 122A and a second central portion 122B coupled to one another via a fabric portion 124. An additional first support portion 126A and a corresponding second support portion 126B on an opposite side may each be angularly coupled to a respective first and second central portion 122A, 122B. A separate back support portion 128 may also be coupled to the central support 122, e.g., either to the central portions 122A, 122B and/or fabric portion 124. Additionally, optional connecting conformable portions 134A, 134B may also be coupled to one or both sides of the back support portion 128 to respective support portions 126A, 126B.

The central portions 122A, 122B as well as support portions 126A, 126B and back support portion 128 may be comprised of a conformable material (e.g., malleable metal such as aluminum or plastics, foams, or any other bendable material) which is relative stiffer than the fabric portion 124 and inner or outer pads. The supporting portions may provide adequate support to a patient when the assembly 120 is placed, e.g., upon a mattress or platform, while enabling the assembly 120 to bend or flex into placement against the patient body when the patient lies upon the assembly 120. The support portions 126A, 126B may incorporate a corresponding first conformable portion 130A and second conformable portion 130B fabricated from a stretchable or distendible material such as a mesh or fabric which is supported by one or more adjustable straps 132 (e.g., straps with hook-and-loop fastening portions) coupling the conformable portions 130A, 130B to their respective support portions 126A, 126B. The flexibility of the conformable portions 130A, 130B may enable the shell assembly to shape or conform more closely to the patient body and may also provide for enhanced comfort.

Because the positioning of the conformable portions 130A, 130B against the patient body may be adjusted, a correlation may be formed between the amount of squeezing or tightening of the assembly 120 upon the patient body and the amount of pressure provided beneath the patient body. For example, if the conformable portions 130A, 130B are squeezed against the patient body a higher pressure can be generated resulting in tightness against the body. This tightness is a variable which can be calculated based on various factors such as the patient's weight, height, etc. Additionally, the pressure can also be correlated to the fluid pressure inside of the inner and/or outer pads.

The back support portion 128 may be coupled via a flexible hinge portion 136 which allows the back support portion 128 to be flexed or angled relative to the central support 122 which may allow the assembly to remain attached securely to the patient as they sit up or lie down. The adjustable straps 132 may also provide stability to the assembly and may also prevent or inhibit the support portions 126A, 126B from falling from the patient body.

Figure 15A:
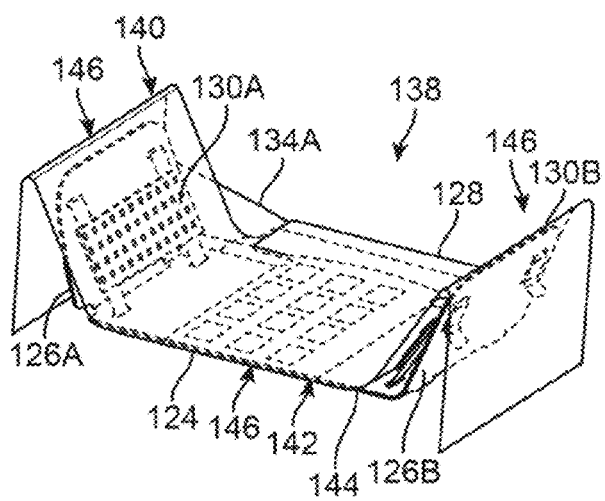
FIGS. 15A and 15B show perspective views of the outer shell assembly having a bladder assembly positioned upon the shell.
Figure 15B:
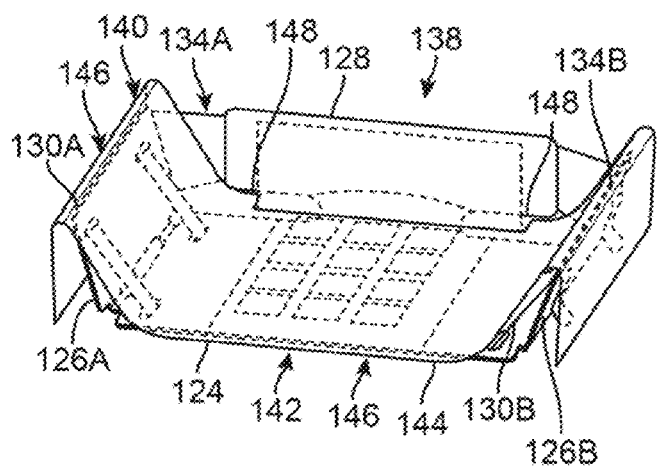

FIGS. 15A and 15B show perspective views of the assembly 120 having a bladder assembly 140 positioned upon the assembly 120 for supporting the patient body along the securement area 138, as described herein. The bladder assembly 140 may comprise the fluid assembly described above generally having an inner pad 142 surrounding the one or more pods 146 and an outer pad 144 which may either encompass the inner pad 142 and pods 146 or which may be laid upon the inner pad 142 and/or pods 146. Moreover, the pods 146 may be positioned along the central portion 122 and/or along one or both conformable portions 130A, 130B. Moreover, bladder assembly 140 may also incorporate one or more relief areas 148 which allow a portion of the bladder assembly 140 to bend or flex along with back support portion 128 when angled relative to the central portion 122.

Another variation of the outer shell support assembly is shown in the perspective view of FIG. 16. The assembly shown may be similarly be used with any of the fluid pad assemblies described herein (not shown for clarity purposes). In this variation, a central portion 122 may similarly be coupled to a back support portion 128 and support portions 126A, 126B. However, the support portions 126A, 126B may be further attached to the central portion 122 via one or more adjustable cords 150A, 150B, 150C, 150D (e.g., bungee cords). The flexible cords may help to maintain a position of support portions 126A, 126B relative to central portion 122, particularly when a patient is lying within or upon the shell assembly and pushing outwardly against the shell. The cords may be attached via attachment points 156 (e.g., along central portion 122) and extend over or through the support portions 126A, 126B through corresponding guide 152 and may further be removably coupled to the assembly via an adjustable mechanism 154 which allows for tension adjustment to cords to correspondingly adjust the amount of force or pressure of the support portions 126A, 126B against the patient's body.

FIGS. 17A to 17C show front and perspective views of yet another variation of the supporting shell assembly (the bladder assembly has been omitted for clarity). This variation may similarly include an outer shell assembly having a central portion 122 with respective support portions 126A, 126B angled relative to the central portion 122. However, this variation may incorporate columns 162 pivotably attached 164 to a platform 160 and extending into connection with one or more openings 166 within respective support portions 126A, 126B. The columns 162 may be pivoted via attachment 164 at a first end and into the one or more openings or receiving channels 166 at a second end to adjust an angle of respective support portions 126A, 126B relative to the central portion 122.

Alternatively, the columns 162 themselves may be adjustable in their height to vary the angle of the support portions 126A, 126B relative to the central portion 122. For example, the columns 162 may be adjustably telescoping to vary their height or the columns 162 may be simply interchangeable between columns of different heights. Moreover, the outer shell assembly shown may incorporate any of the other features described herein in any number of combinations. For instance, the central portion 122 may incorporate a meshed portion and/or a back support portion as well as any number of different combinations of the bladder assembly having the one or more pods positioned variously.

FIG. 18 shows a perspective view of yet another variation where the central portion 122 may incorporate respective composite assemblies 170A, 170B which are adjustably configurable. The composite assembly may generally include a number of individual support elements 172 (e.g., plastic, metal, foam, etc.) which are connected to one another along respective longitudinal axes 176, 178 in an alternating pattern. A tensioning member 174 such as a wire, screw, etc., may be passed through each end of the support elements 172 along the longitudinal axes 176, 178 with a tightening member 180 coupled at the ends of the tensioning member 174. Loosening of the tightening member 180 may allow for the rotation of the individual support elements 172 with respect to one another such that the composite assemblies 170A, 170B may be conformed desirably to the patient's body to closely follow the anatomy. Once a desirable configuration is conformed, the tightening member 180 may be tightened to force or urge the support elements 172 against one another such that the composite assemblies 170A, 170B maintain their configurations.

Figure 19A:
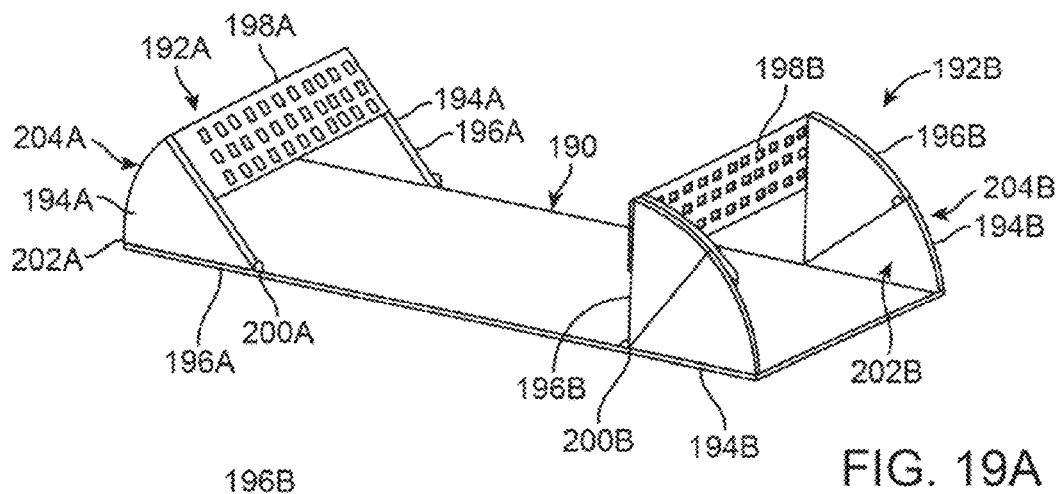
FIGS. 19A to 19C show perspective and side views of yet another outer shell assembly which incorporates a central support portion with respective first and second support portions which are angularly adjustable.
Figure 19B:
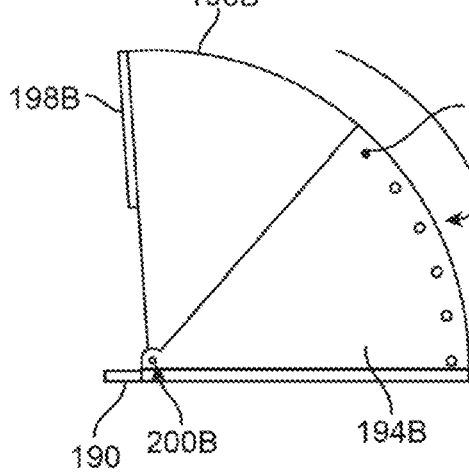
Figure 19C:
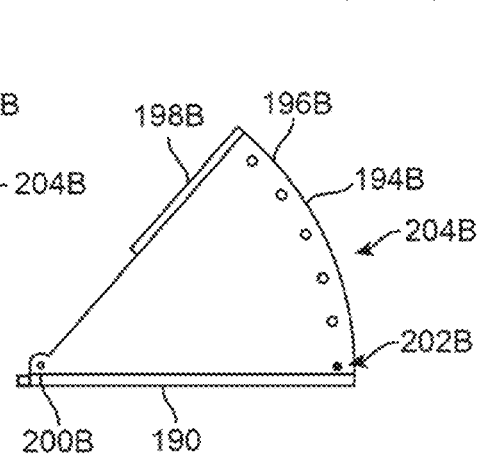

FIGS. 19A to 19C show perspective and side views of yet another outer shell assembly which incorporates a central support portion 190 with respective first and second support portions 192A, 192B. The support portions 192A, 192B may generally comprise first and second angled supports 194A, 194B which are adjustably secured to respective first and second adjustable supports 196A, 196B which may be rotatable about first and second pivots 200A, 200B. The adjustable supports 196A, 196B may each support respective first and second conformable portions 198A, 198B which provide a surface for supporting the bladder assembly against the patient. Moreover, the adjustable supports 196A, 196B may be pivoted relative to the angled supports 194A, 194B to place the conformable portions 198A, 198B into contact with the patient's body. Once suitably positioned, the angled supports 194A, 194B and adjustable supports 196A, 196B may be locked in their configuration via securement pins 202A, 202B through any number of adjustment openings 204A, 204B.

Figure 20A:
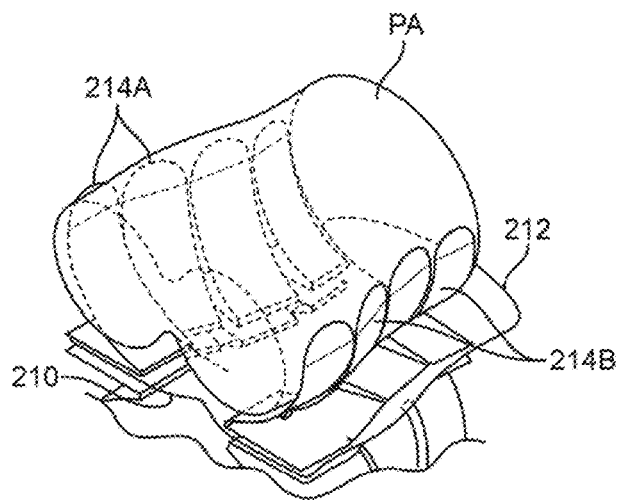
FIGS. 20A and 20B show perspective and side views of another variation where the conforming supports may extend in a curved or arcuate manner from the central support portion.
Figure 20B:
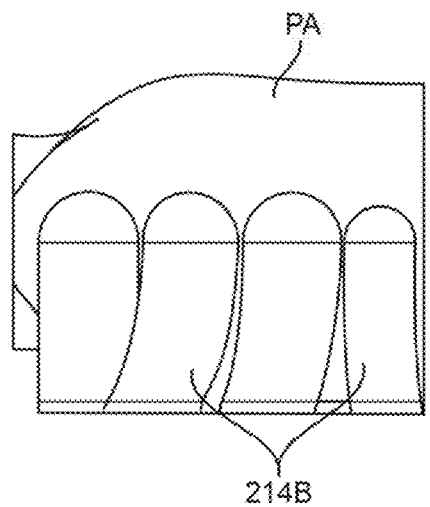

In yet another variation of the outer shell assembly, FIGS. 20A and 20B show perspective and side views of a variation where a central support portion 210 and optional back support portion 212 may include a number of conforming supports 214A, 214B which may extend in a curved or arcuate manner from the central support portion 210 in a shaped shell configuration. The conforming supports 214A, 214B may be shaped to conform more closely to the patient body PA while providing a stiff supporting platform for positioning the bladder assembly against the patient body PA. Moreover, the conforming supports 214A, 214B may be extend in strips or members which are shaped, e.g., like flower petals, and the supports may be secured in place using any number of securement mechanisms, e.g., friction hinge mechanisms, electromechanical locking systems, hydraulic locking systems, magnetic locking systems, electro or magnetoreological locking systems, etc.

Figure 21A:
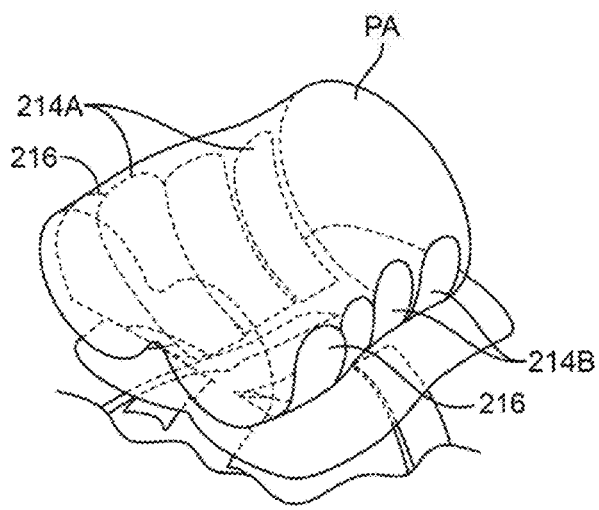
FIGS. 21A and 21B show perspective and side views of another variation where the curved or arcuate conforming supports may overlap one another.
Figure 21B:
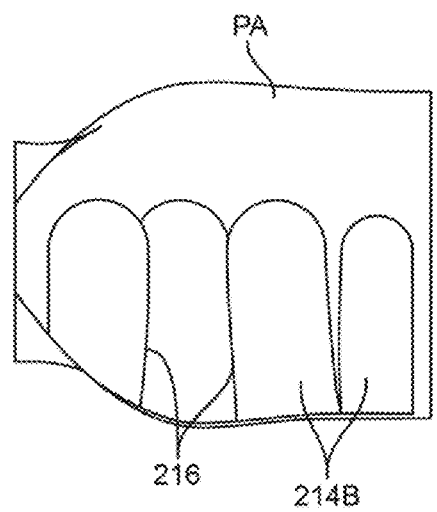

FIGS. 21A and 21 show perspective and side views of another variation similar to the embodiment of FIGS. 20A and 20B. In this variation, one or more of the conforming supports 214A, 214B which are adjacent to one another may define overlapping regions 216 to provide a more contiguous platform.

Figure 22:
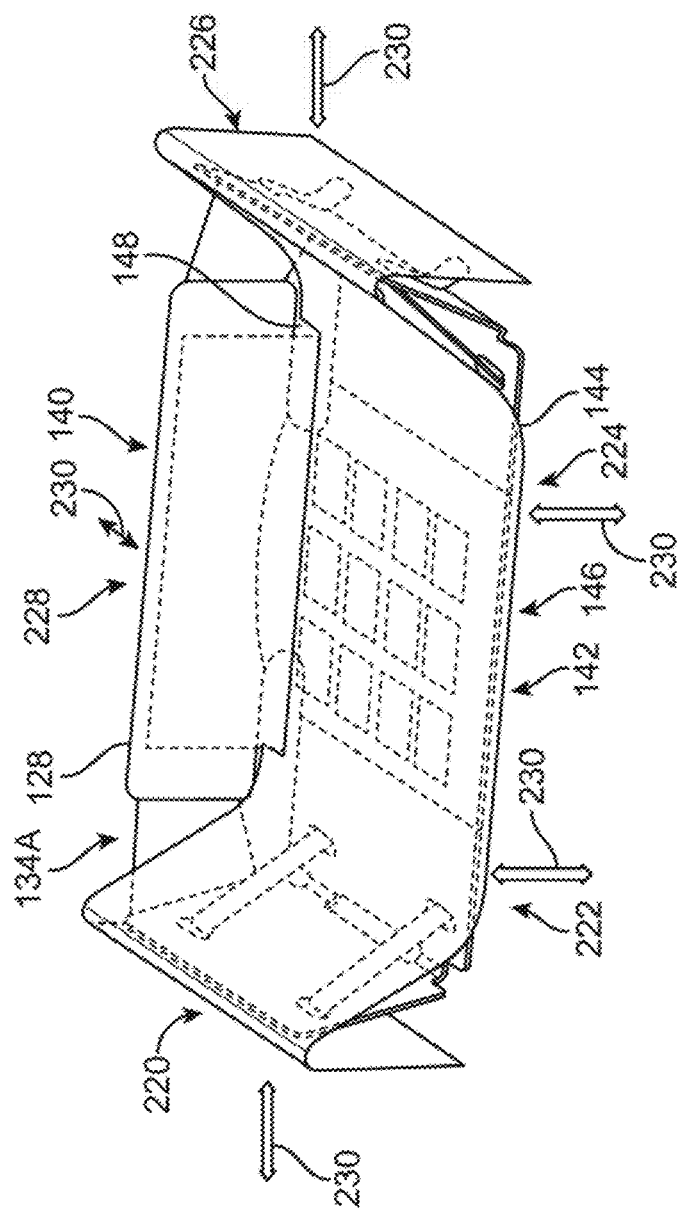
FIG. 22 shows a perspective view of an outer shell variation which may incorporate one or more zones throughout various regions of the shell which may selectively or simultaneously squeeze, vibrate, or otherwise actuate.

Although various outer shell assemblies are disclosed, various features between the different embodiments are intended to be utilized in any number of combinations as desired and as practicable. For example, the variation shown in FIG. 20A may incorporate any number of the support adjustment mechanisms such as columns, rotatable members, etc., in combination for adjusting the supports. Likewise, the features of the outer shell assembly shown in FIG. 22 may be used in combination with any of the outer shell assemblies or pad assemblies described herein. The outer shell assembly may incorporate one or more zones 220, 222, 224, 226, 228 throughout various regions of the shell which may selectively or simultaneously squeeze, vibrate, or otherwise actuate, e.g., in the direction of actuation, vibration, or pulsation 230. These selective zones may vibrate at a selected frequency and/or amplitude and may be actuated at fixed intervals or times.

This actuation 230 can be automated based on a fixed interval/amplitude schedule or can be part of a closed loop system where depending on feedback from certain sensors (e.g., pressure, force, humidity, temperature, etc.) the outer shell can selectively be squeezed or vibrated by a certain amount to ensure that the sensor reading reach a predetermined levels. Moreover, each of the zones can be programmed to vibrate or squeeze in or out selectively or in some combination with each other. These zones may be actuated to squeeze against the patient body just enough to allow for pushing some of the fluid contained within the pad and/or pods, for example, below the sacrum and create a thin layer of fluid below the sacrum.

Moreover, the outer shell may be sized to fit, e.g., more than 95% of a target population, or the outer shell can be designed to be a one-size-fit-all or can be made in two or more different sizes to fit most of the patient population. This sizing can be applied to any of the various outer shell and pad assemblies described herein.

Figure 23A:
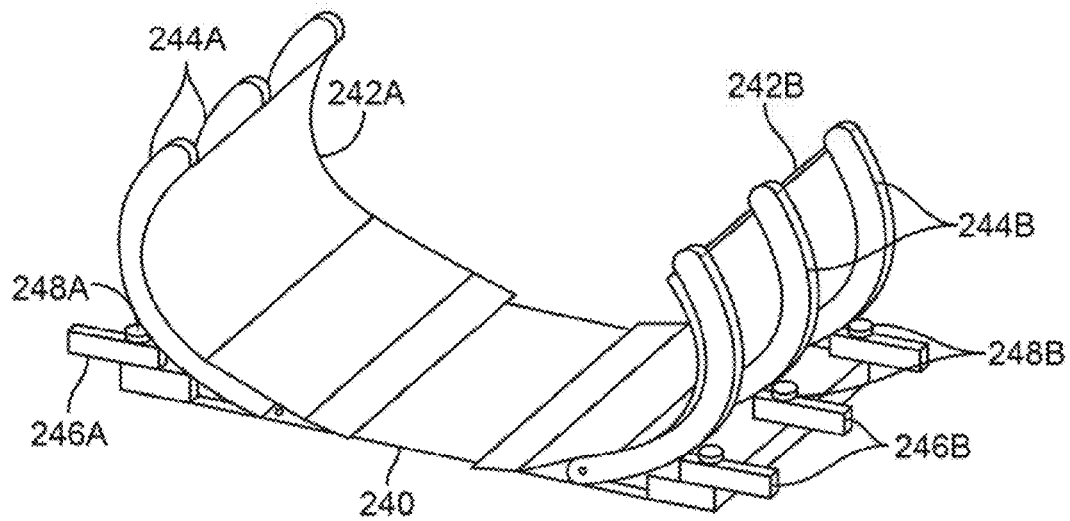
FIGS. 23A and 23B show perspective views of yet another outer shell assembly which has a central support portion with articulating and adjustable support portions.
Figure 23B:
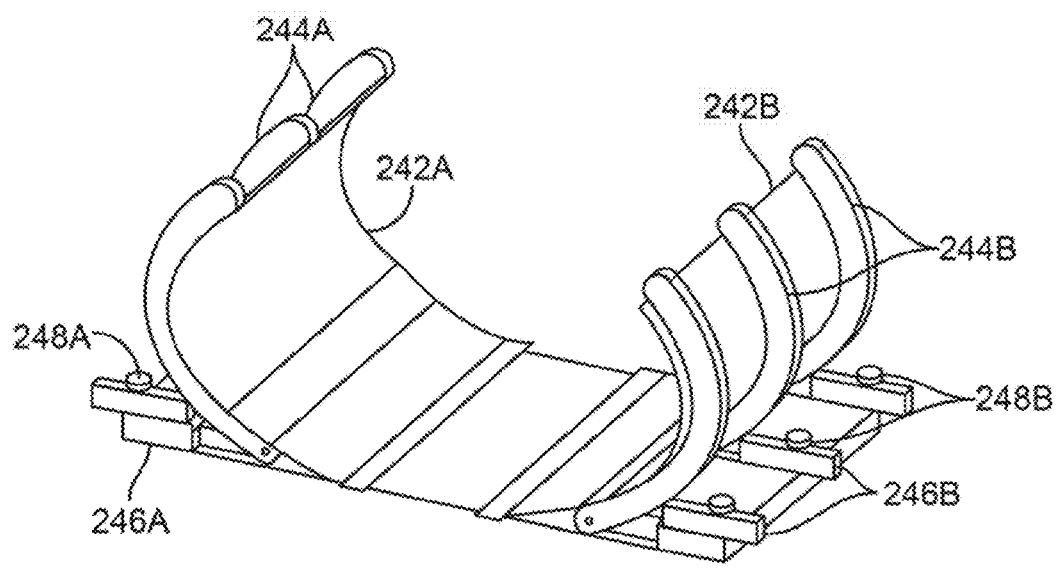

FIGS. 23A and 23B show perspective views of yet another outer shell assembly which has a central support portion 240 with articulating and adjustable support portions. The first and second conforming supports 242A, 242B may be anchored to the central support portion 240 and extend in a curved or arcuate shape for conforming more closely against the patient's body. The supports 242A, 242B may each integrate one or more support members 244A, 244B which are adjacent to respective sliding supports 246A, 246B which may be tuned to push in or out relative to the central support portion 240 to adjust a rotation or bend radius of each support 244A, 244B independently of one another or simultaneously with each support 244A, 244B. Each of the sliding, supports 246A, 246B may be mounted on independent blocks which may be wedged independent to adjust a location of the supports 244A, 244B. Additionally, the sliding supports 246A, 246B may incorporate respective adjustable locks 248A, 248B to secure a position of the support to maintain a configuration of the conforming supports 242A, 242B.

As illustrated in FIG. 23A, the sliding supports 246A, 246B may be extended to position the conforming supports 242A, 242B in an opened configuration, e.g., for receiving a patient body. Once the patient has laid down within the assembly, the sliding supports 246A, 246B may be urged inward to place the conforming supports 242A, 242B against the patient body, as shown in FIG. 23B.

Figure 24A:
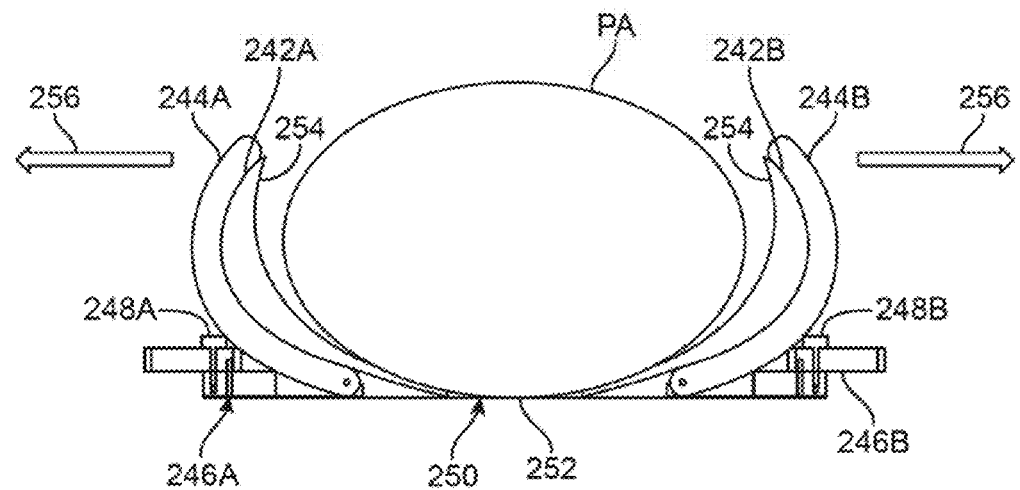
FIGS. 24A and 24B show end views of the conforming supports when urged against the patient body.
Figure 24B:
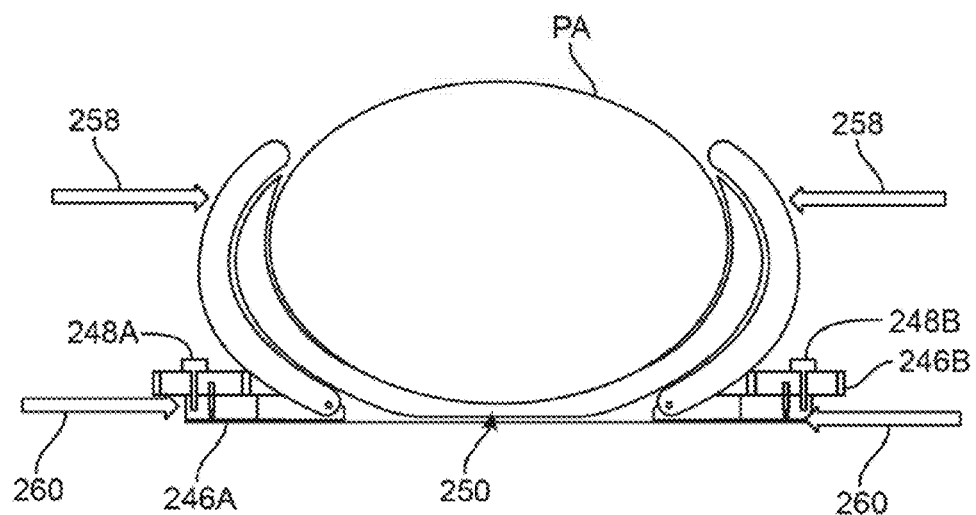

FIGS. 24A and 24B show end views of the conforming supports 242A, 242B when urged against the patient body PA. As previously described, any of the pad assemblies described herein may be used with this outer shell variation. FIG. 24A illustrates how the bladder assembly may bottom out when a patient lies upon the outer pad 250 and is unsupported by the conforming supports 242A, 242B, as shown by the outward direction of support movement 256. As illustrated, the patient body PA may compress the central portion of the pad resulting in a bottomed-out section 252 where the fluid within the pad form bulging sections 254 along the sides when displaced. Yet when the conforming supports 242A, 242B are held or maintained against the patient body PA, as indicated by the direction of support movement 258 and locked in place by the sliding supports 246A, 246B, as indicated by the direction of movement 260, the fluid within the pad 250 along the previously bulging sections 254 may be "squeezed" or redistributed to flow beneath the patient body PA, as shown in FIG. 2413, to eliminate bottom-out section 252 and bulging sections 254.

The redistribution of fluid within the pad 250 may help to reduce any pressure that may result below any bony prominences of the patient body. As the conforming supports 242A, 242B may be rotated or turned to conform more closely to the patient body PA, the fluid distribution may be improved to further reduce pressure beneath the patient.

Figure 25:
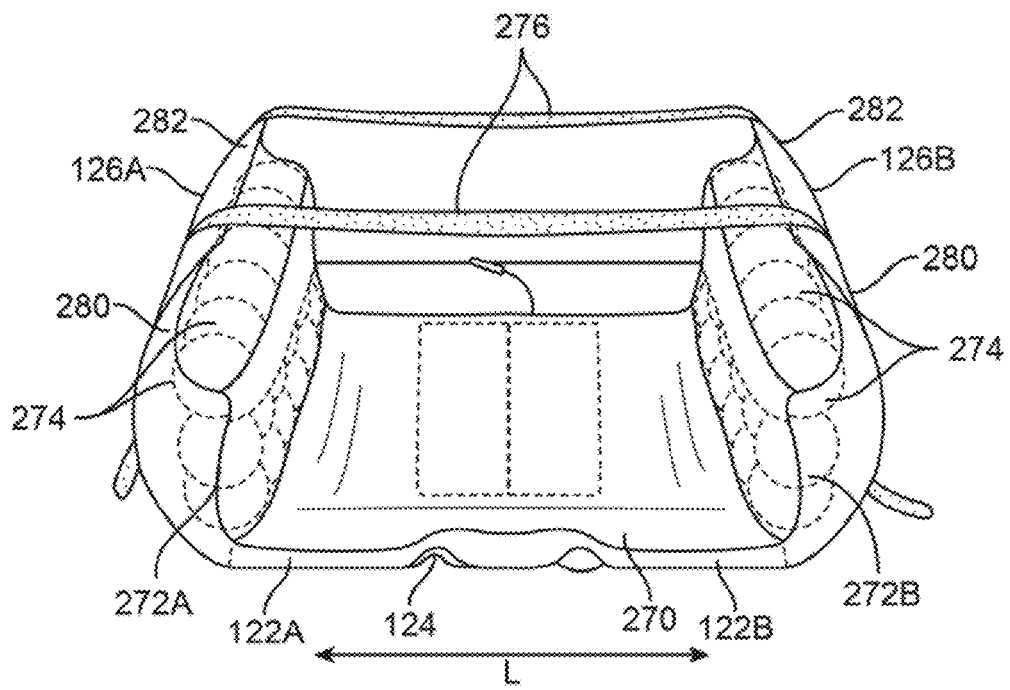
FIG. 25 shows a perspective end view of another outer shell assembly having support portions pivotably attached to respective central portions.

In yet another variation, FIG. 25 shows a perspective end view of another outer shell assembly having support portions 126A, 126B pivotably attached to respective central portions 122A, 122B which may have a fabric portion 124 attached between. This variation may be configured such that the support portions 126A, 126B are arranged to be tangential relative to the patient body placed between. The central portions 122A, 122B and fabric portion 124 may remain flattened beneath the patient's body while the support portions 126A, 126B may extend tangentially and conform to the patient's body. The support portions 126A, 126B may further have a retaining lip or portion 282 pivotably attached via a respective hinge or pivot 280 which are able to be further angled relative to the patient's body, e.g., bent towards the patient's thigh on upon the thigh, to further squeeze or urge fluid within the bladder assembly 270 beneath the patient body and to further prevent fluid from bulging, along the sides of the bladder assembly 270. Alternatively, the retaining lip or portion 282 may omit any hinge or pivot and may simply comprise a flexible extension of the support portions 126A, 126B. Thus, the outer shell assembly and bladder assembly may be designed to mimic the natural shape of the patient's hip region.

To further secure the outer shell assembly to the patient body, one or more adjustable straps 276 may be extend around the open portion of the shell assembly and also around the patient body to ensure that the assembly and retaining lip or portions 282 remain closely conformed and secured to the body.

The variation of the bladder assembly 270 shown placed upon the outer shell assembly may incorporate the inner pad and one or more pods throughout the entire bladder assembly, e.g., along the central portion as well as along the sides. Although, in the variation shown, the inner pads 272A, 272B may be positioned within or beneath or above the assembly 270 along the support portions 126A, 126B. The inner pads 272A, 272B may also contain one or more of the pods 274 within such that the pods 274 are in contact with one another to allow for the transmission of fluid pressure between the pods 274 while remaining contained (or restrained) within their respective inner pads 272A, 272B. The one or more pods 274 may line support portions 126A, 126B and perform the function of achieving conformity with the patient body as well as redirect the fluid below the load bearing region of the patient.

Figure 26:
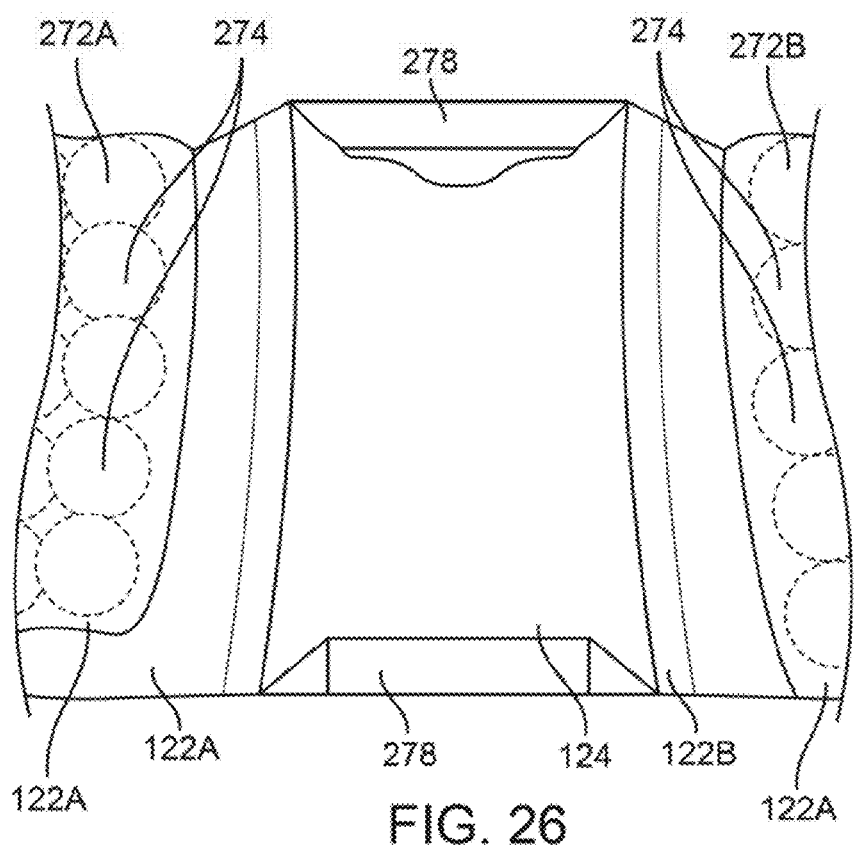
FIG. 26 shows a detail top view of the outer shell assembly having one or more adjustment straps or rails.

While the central portions 122A, 122B may have fabric portion 124 attached between, the two portions 122A, 122B may also be connected by one or more adjustment straps or rails 278 which may limit the movement between two portions 122A, 122B, as shown in the detail top view of FIG. 26 (with part of the bladder assembly 270 removed for clarity). Additionally, the straps or rails 278 may be adjustable to size the distance L between the supports 122A, 122B to more closely conform the shell assembly to the patient body. The distance L may be readjusted to the patient body, e.g., by using a sizing tool, or adjusted after the patient lies down upon the bladder and outer shell assembly using, e.g., a winch type mechanism or any other adjustment mechanism.

Figure 27A:
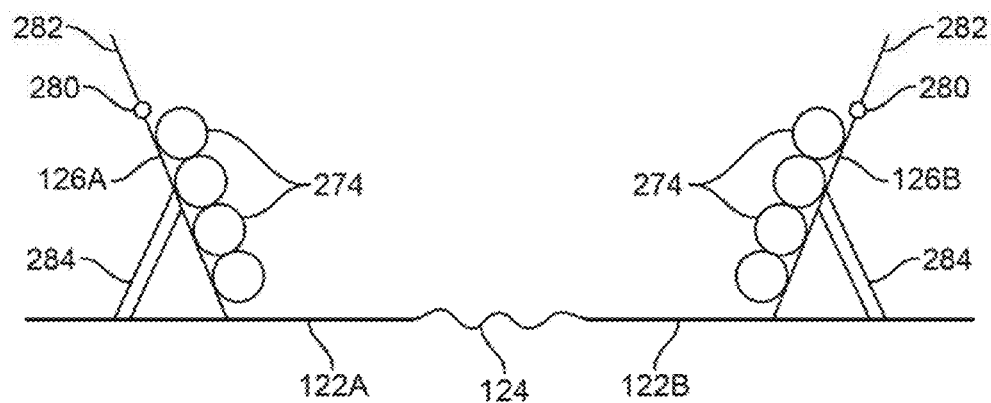
FIGS. 27A and 27B show schematic end views of the outer shell assembly to illustrate how the support portions and retaining lip or portions may be wrapped or placed about a patient's body.
Figure 27B:
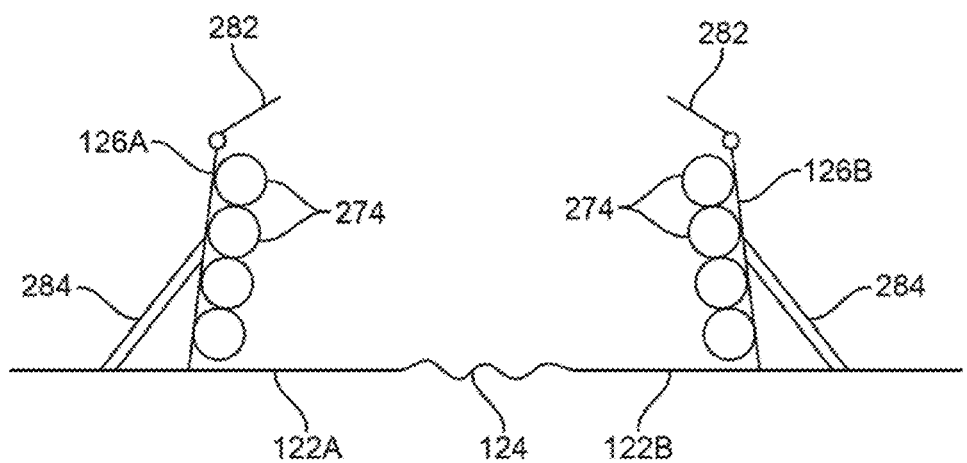

FIGS. 27A and 27B show schematic end views of the outer shell assembly to illustrate how the support portions 126A, 126B and retaining lip or portions 282 may be wrapped or placed about a patient's body. As shown in FIG. 27A, the support portions 126A, 126B may be seen in an open configuration (while optionally supported by supports 284) for receiving a patient body. The one or more pods 274 are shown placed along the support portions 126A, 126B only although they may be placed along the central portion directly beneath the patient's body as well. The inner pads and remaining bladder assembly (such as the outer pad) are not shown only for clarity. Once the patient has been positioned within the assembly, the support portions 126A, 126B may be placed into contact against the sides of the patient's body such that one or more pods 274 are placed into supporting contact as well, as shown in FIG. 27B. The retaining lip or portions 282 may be conformed, bent, or pivoted about their respective hinges (if hinges are used since they may be omitted entirely) such that the portions 282 are further wrapped around the patient's body, such as around their hips or thighs, to further conform against the body as well as to further prevent the fluid pressure or movement of the pods 274 from extending or bulging above the patient's body. The entire assembly may be maintained in position and secured to the patient's body optionally by the use of the one or more adjustable straps 276 described above although the use of straps may be omitted entirely.

The retaining lip or portions 282 ma be configured into various geometries as well. For instance, rather than being flattened segments, the portions 282 may be configured into curved sections where the one or more pods 274 and/or bladder assembly terminate within the curved ends. Moreover, the retaining lip or portions 282 may further incorporate a compression mechanism (such as screw-driven mechanisms, clamps, secondary fluid bladders, etc.) to further increase the compression of the portions 282 upon the pods 274 and/or bladder assembly.

The pressure of fluid within the bladder assembly can be an indicator of the optimal "squeeze" or compression of the support portions 126A, 126B on the patient's body. For instance, based on experimental testing, an optimal pressure range may be determined for each person based on his/her height and weight. If the fluid pressure is too low, this can be an indication of insufficient compression by the support portions 126A, 126B (or insufficient tension in the adjustable straps 276 if the straps are used to squeeze the support portions 126A, 126B upon the patient). Insufficient pressure within the bladder assembly can potentially lead to minimal fluid below the patient leading to bottoming out of the bladder assembly beneath the patient and thus causing localized regions of high pressure. On the other hand, if the fluid pressure within the bladder assembly is too high, this can be an indication of excessive compression of the support portions 126A, 126B upon the patient. Over pressurization can lead to higher pressure readings on the areas where the outer shell assembly is squeezed upon the patient and/or higher pressures on the load bearing region of the body because the downward force on the body is increased. An optimal tension or pressure algorithm can thus be developed for an individual based upon advice of the healthcare provider on the optimal setting.

Such an algorithm can be derived based on a number of parameters but in one example, the following parameters may be taken into account. For example, weight of the patient; height of the patient; width of the patient's hip; gender; estimated sacrum weight; and optimal fluid pressure for the sacrum weight (provided by graphs, lookup tables, or other methods).

Moreover, the pressure of the fluid within the bladder assembly can be measured in different ways as well. For instance, fluid pressure can be determined using, e.g., a pressure gauge which can be removed or attached to the person, a turkey-popper type indicator, any other similar pressure gauges, etc. The internal bladder pressure is simply one indicator which may be used to monitor pressure. Other indicators which may also be used in the alternative or in addition to the internal bladder pressure may optionally utilize measurement of, e.g., strap tension, squeeze force/pressure along the support portions (e.g., by attaching pressure/three sensors), as well as other mechanisms.

Figure 28:
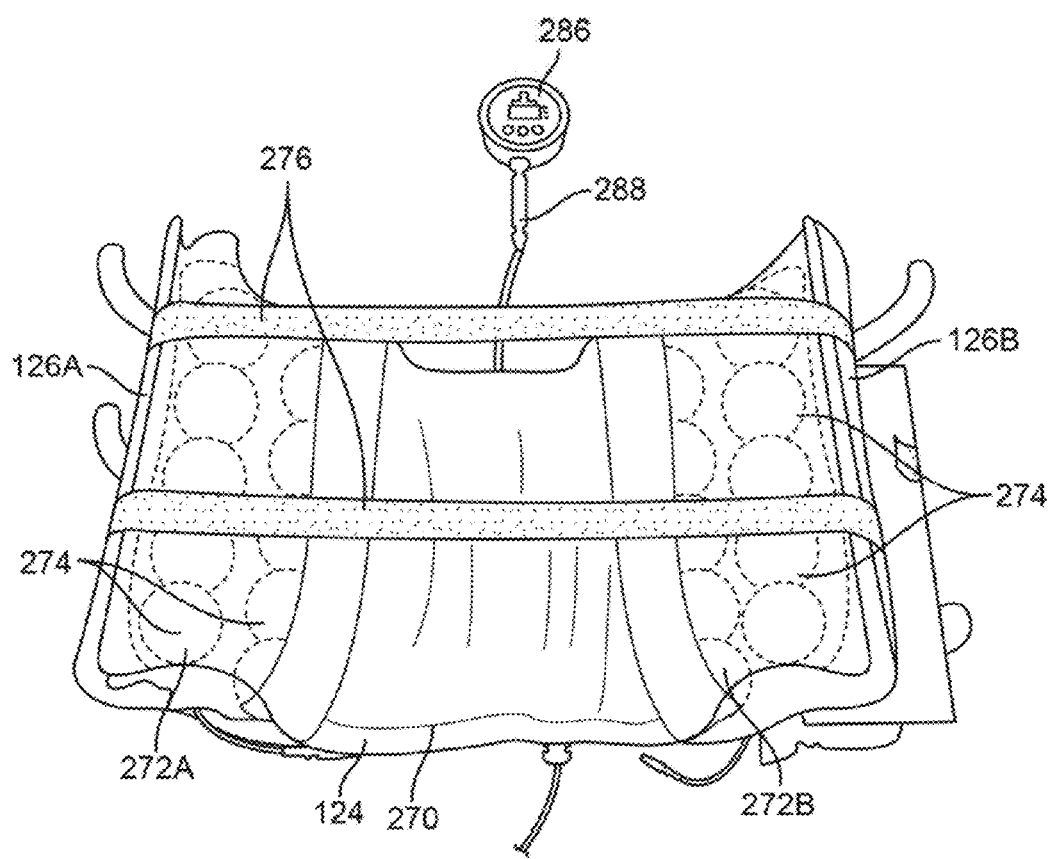
FIG. 28 shows a perspective view of another variation of an outer shell assembly having a bladder assembly incorporating a pressure gauge.

One variation is shown in perspective view of FIG. 28 which illustrates an outer shell assembly having a bladder assembly with a pressure gauge 286 fluidly coupled by a fluid line 288 for determining the pressure of the fluid, for instance, before and/or after the assembly is secured to a patient.

Hence, securing the outer shell assembly to a patient body may be accomplished in number of different ways. One example may include the following steps: (1) the nurse or health care provider may size the patient and notes the weight and height of the patient; (2) the nurse or health care provider may set the distance between the central portions 122A, 122B; (3) the nurse or health care provider may slide the assembly beneath the patient body; (4) the nurse or health care provider may then initially adjust the support portions 126A, 126B against the patient's body while monitoring the pressure indicator until an optimal fluid pressure is reached for the patient based on their parameters such as their height and weight; and (5) the nurse or health care provider may then readjust the outer shell assembly, bladder assembly, or fluid pressure, etc. based on patient comfort and feedback, if provided.

The applications of the devices and methods discussed above are not limited to particular regions of the body such as the sacrum, trochanter, heel, etc. but may include any number of further applications. Modification of the above-described device and methods for carrying out the invention, and variations of aspects of the invention that are obvious to those of skill in the art are intended to be within the scope of the claims.

What is claimed is:

1. An adjustable support assembly, comprising:
a central support portion;
a first support adjustably attached to a first side of the central support;
a second support adjustably attached to a second side of the central support which is opposite to the first side, wherein the first and second supports are angularly adjustable relative to the central support portion;
a fluid filled bladder assembly positioned upon the central support portion and the first and second supports, wherein when a pressure is placed upon the central support portion urges the first and second supports and the fluid filled bladder to conform against a patient body; and
a mesh support positioned between each of the first and second supports and the fluid filled bladder assembly.

2. The assembly of claim 1 wherein the fluid filled bladder comprises an outer fluid pad and an inner pad in communication with the outer fluid pad.

3. The assembly of claim 2 further comprising one or more pods in communication with one another contained within the inner pad.

4. The assembly of claim 2 wherein the one or more pods are positioned along the first support and second support.

5. The assembly of claim 1 further comprising one or more support elements extending between the first and second supports and the central support portion.

6. The assembly of claim 4 wherein the one or more support elements comprise straps, cords, columns, or angled supports.

7. The assembly of claim 1 wherein the central support portion is comprised of a first portion and a second portion adjustably connected to one another.

8. The assembly of claim 7 wherein the first and second portions are adjustably connected to one another via adjustable members.

9. The assembly of claim 1 further comprising a back support portion adjustably attached to a third side of the central support.

10. The assembly of claim 1 wherein the first support and second support each comprise an angularly adjustably retaining portion.

11. The assembly of claim 1 wherein the support assembly further comprises one or more actuation zones in communication with the fluid filled bladder.

12. The assembly of claim 1 further comprising one or more temperature controlled regions within the support assembly.

13. The assembly of claim 1 wherein the first and second supports each comprise a plurality of curved members extending from the central support portion and configured to conform against a subject body.

14. The assembly of claim 1 wherein the first and second supports each comprise a plurality of composite elements rotatably coupled to one another in an alternating manner.

15. The assembly of claim 1 further comprising a fluid pressure measurement indicator fluidly coupled to the fluid filled bladder assembly.

16. The assembly of claim 1 wherein the support assembly is configured to be worn in proximity to a sacrum.

17. An adjustable support assembly, comprising:
an outer shell positionable beneath a portion of a subject's body, wherein the outer shell includes a central support portion, a first support attached to a first side of the central support portion and a second support attached to a second side of the central support portion which is opposite to the first side;
a fluid filled bladder assembly positioned upon the central support portion and the first and second supports: and
a mesh support positioned between each of the first and second supports and the fluid filled bladder assembly,
wherein each support portion is angularly adjustable relative to the central support portion such that securing each support portion against a subject body adjusts a fluid distribution within the bladder assembly.

18. The assembly of claim 17 wherein the fluid filled bladder comprises an outer fluid pad and an inner pad in communication with the outer fluid pad.

19. The assembly of claim 18 further comprising one or more pods in communication with one another contained within the inner pad.

20. The assembly of claim 19 wherein the one or more pods are positioned along the first support and second support.

21. The assembly of claim 17 wherein the central support portion is comprised of a first portion and a second portion adjustably connected to one another.

22. The assembly of claim 21 wherein the first and second portions are adjustably connected to one another via adjustable members.

23. The assembly of claim 17 further comprising one or more support elements extending between the first and second supports and the central support portion.

24. The assembly of claim 23 wherein the one or more support elements comprise straps, cords, columns, or angled supports.

25. The assembly of claim 17 further comprising a back support portion adjustably attached to a third side of the central support.

26. The assembly of claim 17 wherein the support assembly is configured to be worn in proximity to a sacrum.

27. The assembly of claim 17 wherein the first support and second support each comprise an angularly adjustably retaining portion.

28. The assembly of claim 17 wherein the support assembly further comprises one or more actuation zones in communication with the fluid filled bladder.

29. The assembly of claim 17 further comprising one or more temperature controlled regions within the support assembly.

30. The assembly of claim 17 wherein the first and second supports each comprise a plurality of curved members extending from the central support portion and configured to conform against a subject body.

31. The assembly of claim 17 wherein the first and second supports each comprise a plurality of composite elements rotatably coupled to one another in an alternating manner.

32. The assembly of claim 17 further comprising a fluid pressure measurement indicator fluidly coupled to the fluid filled bladder assembly.

33. A method of supporting a region of a body, comprising:
positioning a central support portion beneath the region of the body to be supported;
conforming a first support against a first side of the body, where the first support is adjustably attached to a first side of the central support portion;
conforming a second support against a second side of the body, where the second support is adjustably attached to a second side of the central support portion opposite to the first side;
redistributing a pressure load over the region of the body through a fluid filled outer pad positioned along the central support portion and along each of the first and second supports, wherein a mesh support is positioned between each of the first and second supports and the fluid filled outer pad.

34. The method of claim 33 wherein conforming a first support and conforming a second support each comprise maintaining a position of the first support against the first side of the body and a position of the second support against the second side of the body.

35. The method of claim 34 wherein maintaining comprises securing the position of the first support and the position of the second support via straps, cords, columns, or angled supports.

36. The method of claim 34 further comprising transferring, the pressure load through one or more pods in communication with one another contained within the inner pad.

37. The method of claim 33 further comprising actuating one or more regions of the fluid pad.

38. The method of claim 37 wherein actuating one or more regions comprises alternating a pressure along the one or more regions.

39. The method of claim 33 further comprising monitoring a fluid pressure within the outer pad.

40. The method of claim 39 further comprising adjusting the first support and/or second support against the body based on the fluid pressure.

41. The method of claim 33 wherein positioning comprises placing the central support portion beneath a sacrum of the body.

42. The method of claim 33 wherein redistributing a pressure load comprises transferring the pressure load through the outer fluid pad and an inner pad in communication with the outer pad.

43. The method of claim 33 further comprising controlling a temperature of one or more regions of the body via the support assembly.

* * * * *